(12) United States Patent
Sugiki et al.

(10) Patent No.: US 8,796,485 B2
(45) Date of Patent: Aug. 5, 2014

(54) CASR AGONISTS

(75) Inventors: Masayuki Sugiki, Kawasaki (JP); Toru Okamatsu, Kawasaki (JP); Sayaka Asari, Kawasaki (JP); Yayoi Kawato, Kawasaki (JP); Toshihiro Hatanaka, Kawasaki (JP); Tetsuo Yano, Kawasaki (JP); Yukie Seki, Kawasaki (JP); Naohiro Miyamura, Kawasaki (JP); Hiroaki Nagasaki, Kawasaki (JP); Yuzuru Eto, Kawasaki (JP); Reiko Yasuda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 61 days.

(21) Appl. No.: 13/079,273

(22) Filed: Apr. 4, 2011

(65) Prior Publication Data

US 2011/0251418 A1 Oct. 13, 2011

Related U.S. Application Data

(63) Continuation of application No. PCT/JP2009/067342, filed on Oct. 5, 2009.

(30) Foreign Application Priority Data

Oct. 3, 2008 (JP) ................................. 2008-258003

(51) Int. Cl.
| | |
|---|---|
| *A23L 1/228* | (2006.01) |
| *C07C 237/04* | (2006.01) |
| *C07C 309/51* | (2006.01) |
| *C07F 9/40* | (2006.01) |
| *C07F 9/38* | (2006.01) |
| *A23L 1/305* | (2006.01) |

(52) U.S. Cl.
CPC ............. *C07F 9/3834* (2013.01); *C07C 309/51* (2013.01); *C07F 9/4021* (2013.01); *C07C 237/04* (2013.01); *A23L 1/228* (2013.01); *A23L 1/3051* (2013.01)
USPC ............... 558/190; 560/12; 562/15; 562/444; 562/449; 562/450; 562/52

(58) Field of Classification Search
None
See application file for complete search history.

(56) References Cited

U.S. PATENT DOCUMENTS

| 3,979,447 A | * | 9/1976 | Bernt et al. .................. 562/437 |
| 4,087,331 A | | 5/1978 | Bucolo et al. |
| 4,281,181 A | * | 7/1981 | Nagasawa et al. ............ 562/453 |
| 4,877,727 A | | 10/1989 | Miike et al. |
| 2009/0239310 A1 | | 9/2009 | Ohsu et al. |
| 2009/0239808 A1 | | 9/2009 | Ohsu et al. |
| 2009/0246835 A1 | | 10/2009 | Iwatani et al. |
| 2010/0136197 A1 | | 6/2010 | Eto et al. |

FOREIGN PATENT DOCUMENTS

| EP | 0 152 274 A2 | 8/1985 |
| EP | 0 152 274 A3 | 8/1985 |
| JP | 53-111793 | 9/1978 |
| JP | 56-158745 | 12/1981 |
| JP | 60-164499 | 8/1985 |
| JP | 06-172287 | 6/1994 |
| WO | WO 2007/055388 | 5/2007 |
| WO | WO 2007/055393 | 5/2007 |

OTHER PUBLICATIONS

Cheng et al., Am. J. Physiol Gastrointest Liver Physiol (Apr. 19, 2012), article in press, 31 pages.*
Diarrhea, 2012, http://digestive.niddk.nih.gov/ddiseases/pubs/diarrhea/.*
Miike et al., caplus an 1986:2825.*
G. Szasz, "Reaction-Rate Method for γ-Glutamyltransferase Activity in Serum", Clinical Chemistry, vol. 22, No. 22, 1976, pp. 2051-2055.
R. Lloyd, et al., "α- abd γ-Glutamyl Derivatives of Aminobenzoic Acids", Journal of Medicinal Chemistry, vol. 8, No. 3, 1965, pp. 398-400.
S. Bashir, et al., "Parameterising matrix-assisted laser desorption/ionization (MALDI): strategy for matrix-analyte selection and effect of radical co-additives on analyte peak intensities", Analytica Chimica Acta, vol. 519, No. 2, 2004, pp. 181-187.
M. Wang, et al., Activation of Family C G-protein-coupled Receptors by the Tripeptide Glutathione, Journal of Biological Chemistry, vol. 281, No. 13, 2006, pp. 8864-8870.
Written Opinion of the International Searching Authority mailed Dec. 22, 2009.
U.S. Appl. No. 13/624,254, filed Sep. 21, 2012, Sugiki, et al.
U.S. Appl. No. 13/630,562, filed Sep. 28, 2012, Yasuda, et al.
Office Action in corresponding Japanese application No. 2010-531940, mailed on May 19, 2014. (w/English translation).

* cited by examiner

*Primary Examiner* — Sun Jae Yoo
(74) *Attorney, Agent, or Firm* — Oblon, Spivak, McClelland, Maier & Neustadt, L.L.P.

(57) ABSTRACT

By searching various kinds of compounds having CaSR agonistic activity, the present invention provides CaSR agonistic agents, pharmaceutical compositions, preventive or therapeutic agents for diarrhea and kokumi-imparting agents each of which comprise the compound. More specifically, the present invention provides CaSR agonistic agents, pharmaceutical compositions, preventive or therapeutic agents for diarrhea and kokumi-imparting agents each of which comprise a glutamic acid derivative having CaSR agonistic activity or pharmaceutically acceptable salts thereof.

5 Claims, 2 Drawing Sheets

SEQUENCE LISTING

```
<160> NUMBER OF SEQ ID NOS: 4

<210> SEQ ID NO 1
<211> LENGTH: 4924
<212> TYPE: DNA
<213> ORGANISM: Homo sapiens
<220> FEATURE:
<221> NAME/KEY: CDS
<222> LOCATION: (373)..(3609)
<223> OTHER INFORMATION:

<400> SEQUENCE: 1
caacaggcac ctggctgcag ccaggaagga ccgcacgccc tttcgcgcag gagagtggaa      60
ggagggagct gtttgccagc accgaggtct tgcggcacag gcaacgcttg acctgagtct     120
tgcagaatga aaggcatcac aggaggcctc tgcatgatgt ggcttccaaa gactcaagga     180
ccacccacat tacaagtctg gattgaggaa ggcagaaatg gagattcaaa caccacgtct     240
tctattattt tattaatcaa tctgtagaca tgtgtcccca ctgcagggag tgaactgctc     300 caaggagaa acttctggga gcctccaaac tcctagctgt ctcatccctt gccctggaga     360
gacggcagaa cc atg gca ttt tat agc tgc tgc tgg gtc ctc ttg gca ctc    411
```

```
              Met Ala Phe Tyr Ser Cys Cys Trp Val Leu Leu Ala Leu
              1               5                   10 acc tgg cac acc tct gcc tac ggg cca gac cag cga gcc caa aag aag     459
Thr Trp His Thr Ser Ala Tyr Gly Pro Asp Gln Arg Ala Gln Lys Lys
        15                  20                  25 ggg gac att atc ctt ggg ggc ctc ttt cct att cat ttt gga gta gca     507
Gly Asp Ile Ile Leu Gly Gly Leu Phe Pro Ile His Phe Gly Val Ala
30                  35                  40                  45 gct aaa gat caa gat ctc aaa tca agg ccg gag tct gtg gaa tgt atc     555
Ala Lys Asp Gln Asp Leu Lys Ser Arg Pro Glu Ser Val Glu Cys Ile
                    50                  55                  60 agg tat aat ttc cgt ggg ttt cgc tgg tta cag gct atg ata ttt gcc     603
Arg Tyr Asn Phe Arg Gly Phe Arg Trp Leu Gln Ala Met Ile Phe Ala
                65                  70                  75 ata gag gag ata aac agc agc cca gcc ctt ctt ccc aac ttg acg ctg     651
Ile Glu Glu Ile Asn Ser Ser Pro Ala Leu Leu Pro Asn Leu Thr Leu
            80                  85                  90 gga tac agg ata ttt gac act tgc aac acc gtt tct aag gcc ttg gaa     699
Gly Tyr Arg Ile Phe Asp Thr Cys Asn Thr Val Ser Lys Ala Leu Glu
        95                  100                 105 gcc acc ctg agt ttt gtt gct caa aac aaa att gat tct ttg aac ctt     747
Ala Thr Leu Ser Phe Val Ala Gln Asn Lys Ile Asp Ser Leu Asn Leu
110                 115                 120                 125 gat gag ttc tgc aac tgc tca gag cac att ccc tct acg att gct gtg     795
Asp Glu Phe Cys Asn Cys Ser Glu His Ile Pro Ser Thr Ile Ala Val
                130                 135                 140 gtg gga gca act ggc tca ggc gtc tcc acg gca gtg gca aat ctg ctg     843
Val Gly Ala Thr Gly Ser Gly Val Ser Thr Ala Val Ala Asn Leu Leu
                145                 150                 155 ggg ctc ttc tac att ccc cag gtc agt tat gcc tcc tcc agc aga ctc     891
Gly Leu Phe Tyr Ile Pro Gln Val Ser Tyr Ala Ser Ser Ser Arg Leu
            160                 165                 170 ctc agc aac aag aat caa ttc aag tct ttc ctc cga acc atc ccc aat     939
Leu Ser Asn Lys Asn Gln Phe Lys Ser Phe Leu Arg Thr Ile Pro Asn
        175                 180                 185 gat gag cac cag gcc act gcc atg gca gac atc atc gag tat ttc cgc     987
Asp Glu His Gln Ala Thr Ala Met Ala Asp Ile Ile Glu Tyr Phe Arg
190                 195                 200                 205 tgg aac tgg gtg ggc aca att gca gct gat gac gac tat ggg cgg ccg     1035
Trp Asn Trp Val Gly Thr Ile Ala Ala Asp Asp Asp Tyr Gly Arg Pro
                210                 215                 220 ggg att gag aaa ttc cga gag gaa gct gag gaa agg gat atc tgc atc     1083
Gly Ile Glu Lys Phe Arg Glu Glu Ala Glu Glu Arg Asp Ile Cys Ile
                225                 230                 235 gac ttc agt gaa ctc atc tcc cag tac tct gat gag gaa gag atc cag     1131
Asp Phe Ser Glu Leu Ile Ser Gln Tyr Ser Asp Glu Glu Glu Ile Gln
            240                 245                 250 cat gtg gta gag gtg att caa aat tcc acg gcc aaa gtc atc gtg gtt     1179
His Val Val Glu Val Ile Gln Asn Ser Thr Ala Lys Val Ile Val Val
        255                 260                 265 ttc tcc agt ggc cca gat ctt gag ccc ctc atc aag gag att gtc cgg     1227
Phe Ser Ser Gly Pro Asp Leu Glu Pro Leu Ile Lys Glu Ile Val Arg
270                 275                 280                 285 cgc aat atc acg ggc aag atc tgg ctg gcc agc gag gcc tgg gcc agc     1275
Arg Asn Ile Thr Gly Lys Ile Trp Leu Ala Ser Glu Ala Trp Ala Ser
                290                 295                 300 tcc tcc ctg atc gcc atg cct cag tac ttc cac gtg gtt ggc ggc acc     1323
Ser Ser Leu Ile Ala Met Pro Gln Tyr Phe His Val Val Gly Gly Thr
            305                 310                 315
```

-continued

| | |
|---|---|
| att gga ttc gct ctg aag gct ggg cag atc cca ggc ttc cgg gaa ttc<br>Ile Gly Phe Ala Leu Lys Ala Gly Gln Ile Pro Gly Phe Arg Glu Phe<br>320                                325                                330 | 1371 |
| ctg aag aag gtc cat ccc agg aag tct gtc cac aat ggt ttt gcc aag<br>Leu Lys Lys Val His Pro Arg Lys Ser Val His Asn Gly Phe Ala Lys<br>335                                340                              345 | 1419 |
| gag ttt tgg gaa gaa aca ttt aac tgc cac ctc caa gaa ggt gca aaa<br>Glu Phe Trp Glu Glu Thr Phe Asn Cys His Leu Gln Glu Gly Ala Lys<br>350                                355                            360                            365 | 1467 |
| gga cct tta cct gtg gac acc ttt ctg aga ggt cac gaa gaa agt ggc<br>Gly Pro Leu Pro Val Asp Thr Phe Leu Arg Gly His Glu Glu Ser Gly<br>                                370                              375                            380 | 1515 |
| gac agg ttt agc aac agc tcg aca gcc ttc cga ccc ctc tgt aca ggg<br>Asp Arg Phe Ser Asn Ser Ser Thr Ala Phe Arg Pro Leu Cys Thr Gly<br>                                385                              390                            395 | 1563 |
| gat gag aac atc agc agt gtc gag acc cct tac ata gat tac acg cat<br>Asp Glu Asn Ile Ser Ser Val Glu Thr Pro Tyr Ile Asp Tyr Thr His<br>                            400                              405                            410 | 1611 |
| tta cgg ata tcc tac aat gtg tac tta gca gtc tac tcc att gcc cac<br>Leu Arg Ile Ser Tyr Asn Val Tyr Leu Ala Val Tyr Ser Ile Ala His<br>415                                420                              425 | 1659 |
| gcc ttg caa gat ata tat acc tgc tta cct ggg aga ggg ctc ttc acc<br>Ala Leu Gln Asp Ile Tyr Thr Cys Leu Pro Gly Arg Gly Leu Phe Thr<br>430                                435                              440                            445 | 1707 |
| aat ggc tcc tgt gca gac atc aag aaa gtt gag gcg tgg cag gtc ctg<br>Asn Gly Ser Cys Ala Asp Ile Lys Lys Val Glu Ala Trp Gln Val Leu<br>                                450                              455                            460 | 1755 |
| aag cac cta cgg cat cta aac ttt aca aac aat atg ggg gag cag gtg<br>Lys His Leu Arg His Leu Asn Phe Thr Asn Asn Met Gly Glu Gln Val<br>                                465                              470                            475 | 1803 |
| acc ttt gat gag tgt ggt gac ctg gtg ggg aac tat tcc atc atc aac<br>Thr Phe Asp Glu Cys Gly Asp Leu Val Gly Asn Tyr Ser Ile Ile Asn<br>                                480                              485                            490 | 1851 |
| tgg cac ctc tcc cca gag gat ggc tcc atc gtg ttt aag gaa gtc ggg<br>Trp His Leu Ser Pro Glu Asp Gly Ser Ile Val Phe Lys Glu Val Gly<br>                                495                              500                            505 | 1899 |
| tat tac aac gtc tat gcc aag aag gga gaa aga ctc ttc atc aac gag<br>Tyr Tyr Asn Val Tyr Ala Lys Lys Gly Glu Arg Leu Phe Ile Asn Glu<br>510                                515                              520                            525 | 1947 |
| gag aaa atc ctg tgg agt ggg ttc tcc agg gag gtg ccc ttc tcc aac<br>Glu Lys Ile Leu Trp Ser Gly Phe Ser Arg Glu Val Pro Phe Ser Asn<br>                                530                              535                            540 | 1995 |
| tgc agc cga gac tgc ctg gca ggg acc agg aaa ggg atc att gag ggg<br>Cys Ser Arg Asp Cys Leu Ala Gly Thr Arg Lys Gly Ile Ile Glu Gly<br>                                545                              550                            555 | 2043 |
| gag ccc acc tgc tgc ttt gag tgt gtg gag tgt cct gat ggg gag tat<br>Glu Pro Thr Cys Cys Phe Glu Cys Val Glu Cys Pro Asp Gly Glu Tyr<br>                                560                              565                            570 | 2091 |
| agt gat gag aca gat gcc agt gcc tgt aac aag tgc cca gat gac ttc<br>Ser Asp Glu Thr Asp Ala Ser Ala Cys Asn Lys Cys Pro Asp Asp Phe<br>575                                580                              585 | 2139 |
| tgg tcc aat gag aac cac acc tcc tgc att gcc aag gag atc gag ttt<br>Trp Ser Asn Glu Asn His Thr Ser Cys Ile Ala Lys Glu Ile Glu Phe<br>590                                595                              600                            605 | 2187 |
| ctg tcg tgg acg gag ccc ttt ggg atc gca ctc acc ctc ttt gcc gtg<br>Leu Ser Trp Thr Glu Pro Phe Gly Ile Ala Leu Thr Leu Phe Ala Val<br>                                610                              615                            620 | 2235 |
| ctg ggc att ttc ctg aca gcc ttt gtg ctg ggt gtg ttt atc aag ttc<br>Leu Gly Ile Phe Leu Thr Ala Phe Val Leu Gly Val Phe Ile Lys Phe<br>                                625                              630                            635 | 2283 |

```
cgc aac aca ccc att gtc aag gcc acc aac cga gag ctc tcc tac ctc      2331
Arg Asn Thr Pro Ile Val Lys Ala Thr Asn Arg Glu Leu Ser Tyr Leu
            640             645                 650 ctc ctc ttc tcc ctg ctc tgc tgc ttc agc tcc ctg ttc ttc atc          2379
Leu Leu Phe Ser Leu Leu Cys Cys Phe Ser Ser Leu Phe Phe Ile
        655                 660                 665 ggg gag ccc cag gac tgg acg tgc cgc ctg cgc cag ccg gcc ttt ggc      2427
Gly Glu Pro Gln Asp Trp Thr Cys Arg Leu Arg Gln Pro Ala Phe Gly
670             675                 680                 685 atc agc ttc gtg ctc tgc atc tca tgc atc ctg gtg aaa acc aac cgt      2475
Ile Ser Phe Val Leu Cys Ile Ser Cys Ile Leu Val Lys Thr Asn Arg
            690                 695                 700 gtc ctc ctg gtg ttt gag gcc aag atc ccc acc agc ttc cac cgc aag      2523
Val Leu Leu Val Phe Glu Ala Lys Ile Pro Thr Ser Phe His Arg Lys
        705                 710                 715 tgg tgg ggg ctc aac ctg cag ttc ctg ctg gtt ttc ctc tgc acc ttc      2571
Trp Trp Gly Leu Asn Leu Gln Phe Leu Leu Val Phe Leu Cys Thr Phe
            720                 725                 730 atg cag att gtc atc tgt gtg atc tgg ctc tac acc gcg ccc ccc tca      2619
Met Gln Ile Val Ile Cys Val Ile Trp Leu Tyr Thr Ala Pro Pro Ser
        735                 740                 745 agc tac cgc aac cag gag ctg gag gat gag atc atc ttc atc acg tgc      2667
Ser Tyr Arg Asn Gln Glu Leu Glu Asp Glu Ile Ile Phe Ile Thr Cys
750             755                 760                 765 cac gag ggc tcc ctc atg gcc ctg ggc ttc ctg atc ggc tac acc tgc      2715
His Glu Gly Ser Leu Met Ala Leu Gly Phe Leu Ile Gly Tyr Thr Cys
            770                 775                 780 ctg ctg gct gcc atc tgc ttc ttc ttt gcc ttc aag tcc cgg aag ctg      2763
Leu Leu Ala Ala Ile Cys Phe Phe Phe Ala Phe Lys Ser Arg Lys Leu
        785                 790                 795 ccg gag aac ttc aat gaa gcc aag ttc atc acc ttc agc atg ctc atc      2811
Pro Glu Asn Phe Asn Glu Ala Lys Phe Ile Thr Phe Ser Met Leu Ile
800             805                 810 ttc ttc atc gtc tgg atc tcc ttc att cca gcc tat gcc agc acc tat      2859
Phe Phe Ile Val Trp Ile Ser Phe Ile Pro Ala Tyr Ala Ser Thr Tyr
            815                 820                 825 ggc aag ttt gtc tct gcc gta gag gtg att gcc atc ctg gca gcc agc      2907
Gly Lys Phe Val Ser Ala Val Glu Val Ile Ala Ile Leu Ala Ala Ser
830             835                 840                 845 ttt ggc ttg ctg gcg tgc atc ttc ttc aac aag atc tac atc att ctc      2955
Phe Gly Leu Leu Ala Cys Ile Phe Phe Asn Lys Ile Tyr Ile Ile Leu
            850                 855                 860 ttc aag cca tcc cgc aac acc atc gag gag gtg cgt tgc agc acc gca      3003
Phe Lys Pro Ser Arg Asn Thr Ile Glu Glu Val Arg Cys Ser Thr Ala
        865                 870                 875 gct cac gct ttc aag gtg gct gcc cgg gcc acg ctg cgc cgc agc aac      3051
Ala His Ala Phe Lys Val Ala Ala Arg Ala Thr Leu Arg Arg Ser Asn
880             885                 890 gtc tcc cgc aag cgg tcc agc agc ctt gga ggc tcc acg gga tcc acc      3099
Val Ser Arg Lys Arg Ser Ser Ser Leu Gly Gly Ser Thr Gly Ser Thr
            895                 900                 905 ccc tcc tcc tcc atc agc agc aag agc aac agc gaa gac cca ttc cca      3147
Pro Ser Ser Ser Ile Ser Ser Lys Ser Asn Ser Glu Asp Pro Phe Pro
910                 915                 920                 925 cag ccc gag agg cag aag cag cag cag ccg ctg gcc cta acc cag caa      3195
Gln Pro Glu Arg Gln Lys Gln Gln Gln Pro Leu Ala Leu Thr Gln Gln
            930                 935                 940 gag cag cag cag cag ccc ctg acc ctc cca cag cag caa cga tct cag      3243
Glu Gln Gln Gln Gln Pro Leu Thr Leu Pro Gln Gln Gln Arg Ser Gln
```

```
            945                 950                 955
cag cag ccc aga tgc aag cag aag gtc atc ttt ggc agc ggc acg gtc    3291
Gln Gln Pro Arg Cys Lys Gln Lys Val Ile Phe Gly Ser Gly Thr Val
        960                 965                 970 acc ttc tca ctg agc ttt gat gag cct cag aag aac gcc atg gcc cac    3339
Thr Phe Ser Leu Ser Phe Asp Glu Pro Gln Lys Asn Ala Met Ala His
    975                 980                 985 agg aat tct acg cac cag aac tcc ctg gag gcc cag aaa agc agc gat    3387
Arg Asn Ser Thr His Gln Asn Ser Leu Glu Ala Gln Lys Ser Ser Asp
990                 995                 1000                1005 acg ctg acc cga cac cag cca tta ctc ccg ctg cag tgc ggg gaa        3432
Thr Leu Thr Arg His Gln Pro Leu Leu Pro Leu Gln Cys Gly Glu
            1010                1015                1020 acg gac tta gat ctg acc gtc cag gaa aca ggt ctg caa gga cct        3477
Thr Asp Leu Asp Leu Thr Val Gln Glu Thr Gly Leu Gln Gly Pro
            1025                1030                1035 gtg ggt gga gac cag cgg cca gag gtg gag gac cct gaa gag ttg        3522
Val Gly Gly Asp Gln Arg Pro Glu Val Glu Asp Pro Glu Glu Leu
            1040                1045                1050 tcc cca gca ctt gta gtg tcc agt tca cag agc ttt gtc atc agt        3567
Ser Pro Ala Leu Val Val Ser Ser Ser Gln Ser Phe Val Ile Ser
            1055                1060                1065 ggt gga ggc agc act gtt aca gaa aac gta gtg aat tca taa            3609
Gly Gly Gly Ser Thr Val Thr Glu Asn Val Val Asn Ser
            1070                1075 aatggaagga gaagactggg ctagggagaa tgcagagagg tttcttgggg tcccagggaa  3669
gaggaatcgc cccagactcc tttcctctga ggaagaaggg ataatagaca catcaaatgc  3729
cccgaattta gtcacaccat cttaaatgac agtgaattga cccatgttcc ctttaaaatt  3789
aaaaaaaaga gagccttgt gtttctgtgg ttgcatttgt caaagcattg agatctccac    3849
ggtcagattt gctgttcacc cacatctaat gtctcttcct ctgttctatc ccacccaaca  3909
gctcagagat gaaactatgg ctttaaacta ccctccagag tgtgcagact gatgggacat  3969
caaatttgcc accactagag ctgagagtct gaaagacaga atgtcaccag tcctgcccaa  4029
tgccttgaca acagactgaa ttttaaatgt tcacaacata aggagaatgt atctcctcct  4089
atttatgaaa accatatgat attttgtctc ctacctgctg ctgctattat gtaacatcca  4149
gaaggtttgc acccctccta taccatatgt ctgcttctgt ccaggacatg atactgatgc  4209
catgtttaga ttccaggatc acaagaatca cctcaaattg ttaggaaggg actgcataaa  4269
ccaatgagct gtatctgtaa ttaatattcc tatatgtagc tttatcctta ggaaaatgct  4329
tctgttgtaa tagtccatgg acaatataaa ctgaaaaatg tcagtctggt ttatataagg  4389
cagtattatt gagctctatt tccccacccc actatcctca ctcccataag ctaagcctta  4449
tgtgagcccc ttcagggact caagggtcca gaagtccctc ccatctctac cccaaagaat  4509
tcctgaagcc agatccaccc tatccctgta cagagtaagt tctcaattat tggcctgcta  4569
atagctgcta gggtaggaaa gcgtggttcc aagaaagatc caccctcaaa tgtcagagct  4629
atgttccctc cagcagtggt attaatactg ccggtcaccc aggctctgga gccagagaga  4689
cagaccgggg ttcaagccat ggcttcgtca tttgcaagct gagtgactgt aggcagggaa  4749
ccttaacctc tctaagccac agcttcttca tctttaaaat aaggataata atcattcttt  4809
cccctcagag ctcttatgtg gattaaacga gataatgtat ataaagtact ttagcctggt  4869
acctagcaca caataagcat tcaataaata ttagttaata ttattaaaaa aaaaa        4924
```

<210> SEQ ID NO 2
<211> LENGTH: 1078
<212> TYPE: PRT
<213> ORGANISM: Homo sapiens

<400> SEQUENCE: 2

```
Met Ala Phe Tyr Ser Cys Cys Trp Val Leu Leu Ala Leu Thr Trp His
 1               5                  10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
210                 215                 220

Lys Phe Arg Glu Glu Ala Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Asn Ile
        275                 280                 285

Thr Gly Lys Ile Trp Leu Ala Ser Glu Ala Trp Ala Ser Ser Ser Leu
        290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335

Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
        355                 360                 365

Pro Val Asp Thr Phe Leu Arg Gly His Glu Glu Ser Gly Asp Arg Phe
        370                 375                 380
```

-continued

```
Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
                500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Val Pro Phe Ser Asn Cys Ser Arg
530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
            595                 600                 605

Thr Glu Pro Phe Gly Ile Ala Leu Thr Leu Phe Ala Val Leu Gly Ile
610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Ser Leu Phe Phe Ile Gly Glu Pro
                660                 665                 670

Gln Asp Trp Thr Cys Arg Leu Arg Gln Pro Ala Phe Gly Ile Ser Phe
            675                 680                 685

Val Leu Cys Ile Ser Cys Ile Leu Val Lys Thr Asn Arg Val Leu Leu
            690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys His Glu Gly
            755                 760                 765

Ser Leu Met Ala Leu Gly Phe Leu Ile Gly Tyr Thr Cys Leu Leu Ala
            770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
```

```
                    805                 810                 815
Val Trp Ile Ser Phe Ile Pro Ala Tyr Ala Ser Thr Tyr Gly Lys Phe
                820                 825                 830

Val Ser Ala Val Glu Val Ile Ala Ile Leu Ala Ala Ser Phe Gly Leu
                835                 840                 845

Leu Ala Cys Ile Phe Phe Asn Lys Ile Tyr Ile Ile Leu Phe Lys Pro
    850                 855                 860

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
                900                 905                 910

Ser Ile Ser Ser Lys Ser Asn Ser Glu Asp Pro Phe Pro Gln Pro Glu
    915                 920                 925

Arg Gln Lys Gln Gln Gln Pro Leu Ala Leu Thr Gln Gln Glu Gln Gln
930                 935                 940

Gln Gln Pro Leu Thr Leu Pro Gln Gln Arg Ser Gln Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala His Arg Asn Ser
                980                 985                 990

Thr His Gln Asn Ser Leu Glu Ala  Gln Lys Ser Ser Asp  Thr Leu Thr
            995                 1000                 1005

Arg His  Gln Pro Leu Leu Pro  Leu Gln Cys Gly Glu  Thr Asp Leu
    1010                 1015                 1020

Asp Leu  Thr Val Gln Glu Thr  Gly Leu Gln Gly Pro  Val Gly Gly
    1025                 1030                 1035

Asp Gln  Arg Pro Glu Val Glu  Asp Pro Glu Glu Leu  Ser Pro Ala
    1040                 1045                 1050

Leu Val  Val Ser Ser Ser Gln  Ser Phe Val Ile Ser  Gly Gly Gly
    1055                 1060                 1065

Ser Thr Val Thr Glu Asn Val  Val Asn Ser
    1070                 1075

<210> SEQ ID NO 3
<211> LENGTH: 49
<212> TYPE: DNA
<213> ORGANISM: Artificial
<220> FEATURE:
<223> OTHER INFORMATION: primer

<400> SEQUENCE: 3
actaatacga ctcactatag ggaccatggc attttatagc tgctgctgg                  49

<210> SEQ ID NO 4
<211> LENGTH: 29
<212> TYPE: DNA
<213> ORGANISM: Artificial
<220> FEATURE:
<223> OTHER INFORMATION: primer

<400> SEQUENCE: 4
ttatgaattc actacgtttt ctgtaacag                                        29
```

CASR AGONISTS

TECHNICAL FIELD OF THE INVENTION

The present invention relates to glutamic acid derivatives having CaSR agonistic activity or pharmaceutically acceptable salts thereof; and CaSR agonistic agents, pharmaceutical compositions, preventive or therapeutic agents for diarrhea and kokumi-imparting agents each of which comprise the glutamic acid derivative or pharmaceutically acceptable salts thereof as an active ingredient.

BACKGROUND OF THE INVENTION

A calcium sensing receptor (CaSR) is also called a calcium receptor, and such receptor signals regulate various functions in vivo. Thus, there is a possibility that substances having CaSR agonistic activity are useful for treating or preventing various diseases and also useful as kokumi-imparting agents. Patent Literature 1 discloses a method for screening for a kokumi-imparting substance and a kokumi-imparting agent containing a kokumi-imparting substance obtained by the screening method. In the literature, it is found that various low molecular peptides have CaSR agonistic activity. Based on this finding, it discloses that it becomes possible to provide a kokumi-imparting agent which can impart "kokumi", the taste that cannot be expressed with five basic tastes of sweetness, saltiness, sourness, bitterness and umami, and the taste that enhances marginal tastes of the basic tastes, such as thickness, growth (mouthfullness), continuity, and harmony.

Meanwhile, it is known that a γ-glutamyl anilide derivative can be used for measuring the enzyme activity since it becomes a substrate of γ-glutamyl transferase (refer to Non-patent Literature 1 and Patent Literature 2). However, there is no reference that discloses the relationship of a γ-glutamyl anilide derivative with "a calcium sensing receptor (CaSR) or a G-protein-coupled receptor", "kokumi" and "diarrhea or hyperparathyroidism", each of which is disclosed in the present invention. The main use of some publicly known compounds among 3-sulfonic acid, 3-carboxylic acid and 3-nitro derivatives, each of which are particularly preferable in the present invention, are a substrate in measuring the enzyme activity of γ-glutamyl transferase. As other uses, it is slightly known that it is used as an antimicrobial agent or an antiallergic agent (refer to Non-patent Literature 2 and Patent Literature 3) and as a reagent for mass spectrometry (refer to Non-patent Literature 3). Further, it is known that examples of a compound activating CaSR include cinacalcet and similar synthetic low molecular compounds, and γ-glutamyl peptide derivatives such as glutathione (refer to Patent Literature 4 and Non-patent Literature 4). However, they are structurally different from glutamic acid derivatives of the present invention.

Therefore, it is expected to provide more excellent kokumi-imparting agents by searching more varieties of compounds having CaSR agonistic activity. It is also expected to provide CaSR agonistic agents, pharmaceutical compositions and preventive or therapeutic agents for diarrhea.

Patent Literature 1: WO 2007/055393 A1
Patent Literature 2: U.S. Pat. No. 4,087,331
Patent Literature 3: JP-A 06-172287
Patent Literature 4: WO 2007/055388 A2
Non-patent Literature 1: Clinical Chemistry, 22, 2051 (1976)
Non-patent Literature 2: Journal of Medicinal Chemistry (1965), 8(3), 398-400
Non-patent Literature 3: Analytica Chimica Acta (2004), 519 (2), 181-187
Non-patent Literature 4: Journal of Biological Chemistry (2006), 281(13), 8864-70

DISCLOSURE OF THE INVENTION

Problems to be Solved by the Invention

The object of the present invention is, by searching various kinds of compounds having CaSR agonistic activity, to provide CaSR agonistic agents, pharmaceutical compositions, preventive or therapeutic agents for diarrhea and kokumi-imparting agents each of which comprise the compound.

Means for Solving the Problems

The inventors searched compounds having CaSR agonistic activity, and surprisingly, they found that various γ-glutamic acid derivatives and analogues thereof (hereinafter referred to as glutamic acid derivatives) have an excellent CaSR agonistic activity. Further, they found that the glutamic acid derivatives having CaSR agonistic activity or pharmaceutically acceptable salts thereof can be useful as CaSR agonistic agents, pharmaceutical compositions, preventive or therapeutic agents for diarrhea or kokumi-imparting agents. The present invention has been completed based on these findings.

Namely, the present invention provides a glutamic acid derivative of the following formula (I) or pharmaceutically acceptable salts thereof:

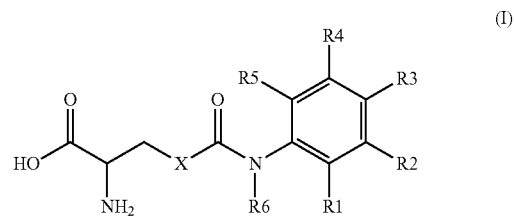

wherein $R_1$ and $R_3$-$R_5$ are each independently selected from the group consisting of a hydrogen atom, a halogeno group, a hydroxyl group, a nitro group, an amino group, an alkyl group having 1 to 6 carbon atoms which may have a substituent(s), an alkoxy group having 1 to 6 carbon atoms which may have a substituent(s) and a mono- or di-alkylamino group having 1 to 6 carbon atoms which may have a substituent(s); $R_2$ is selected from the group consisting of a nitro group, a sulfonic acid group,

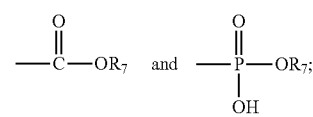

$R_6$ and $R_7$ each independently represent a hydrogen atom or an alkyl group having 1 to 6 carbon atoms which may have a substituent(s); and X represents a methylene group or an oxygen atom, provided that the following compounds (i)-(iv) are excluded:
(i) a compound wherein X is a methylene group, $R_2$ is a sulfonic acid group, and each of $R_1$ and $R_3$-$R_6$ is a hydrogen atom;
(ii) a compound wherein X is a methylene group, $R_2$ is a sulfonic acid group, each of $R_1$ and $R_4$-$R_6$ is a hydrogen atom, and $R_3$ is a nitro group;

(iii) a compound wherein X is a methylene group, $R_2$ is a nitro group, and each of $R_1$ and $R_3$-$R_6$ is a hydrogen atom; and
(iv) a compound wherein X is a methylene group, $R_2$ is

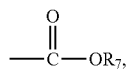

each of $R_1$ and $R_4$-$R_6$ is a hydrogen atom, $R_3$ is a hydrogen atom, a nitro group, a hydroxyl group, an amino group, a diethylamino group or a di-n-propylamino group, and $R_7$ is a hydrogen atom or a methyl group.

The present invention also provides a glutamic acid derivative of the following formula (I) or pharmaceutically acceptable salts thereof:

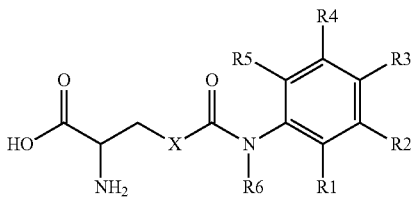

(I)

wherein $R_2$, $R_4$ and $R_5$ are each independently selected from the group consisting of a hydrogen atom, a halogeno group, a hydroxyl group, a nitro group, an amino group, an alkyl group having 1 to 6 carbon atoms which may have a substituent(s), an alkoxy group having 1 to 6 carbon atoms which may have a substituent(s) and a mono- or di-alkylamino group having 1 to 6 carbon atoms which may have a substituent(s); either $R_1$ or $R_3$ is a sulfonic acid group and the other is selected from the group consisting of a hydrogen atom, a halogeno group, a hydroxyl group, a nitro group, an amino group, an alkyl group having 1 to 6 carbon atoms which may have a substituent(s), an alkoxy group having 1 to 6 carbon atoms which may have a substituent(s) and a mono- or di-alkylamino group having 1 to 6 carbon atoms which may have a substituent(s); $R_6$ and $R_7$ each independently represent a hydrogen atom or an alkyl group having 1 to 6 carbon atoms which may have a substituent(s); and X represents a methylene group or an oxygen atom,
provided that the following compound is excluded:
a compound wherein X is a methylene group, $R_1$ is a sulfonic acid group, and each of $R_2$-$R_6$ is a hydrogen atom.

The present invention also provides a glutamic acid derivative of the following formula (I) or pharmaceutically acceptable salts thereof:

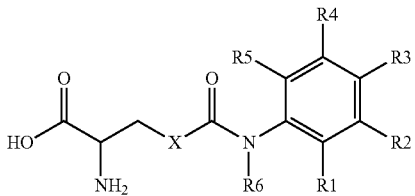

(I)

wherein $R_1$ and $R_3$-$R_5$ are each independently selected from the group consisting of a hydrogen atom, a halogeno group, a hydroxyl group, a nitro group, an amino group, an alkyl group having 1 to 6 carbon atoms which may have a substituent(s), an alkoxy group having 1 to 6 carbon atoms which may have a substituent(s) and a mono- or di-alkylamino group having 1 to 6 carbon atoms which may have a substituent(s); $R_2$ is selected from the group consisting of a nitro group, a sulfonic acid group,

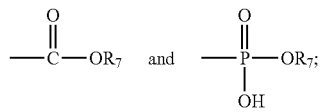

$R_6$ represents a hydroxyl group; $R_7$ represents a hydrogen atom or an alkyl group having 1 to 6 carbon atoms which may have a substituent(s); and X represents a methylene group or an oxygen atom.

The present invention also provides a pharmaceutical composition comprising a glutamic acid derivative of the following formula (I) or pharmaceutically acceptable salts thereof:

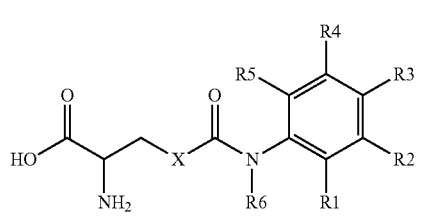

(I)

wherein $R_1$ and $R_3$-$R_5$ are each independently selected from the group consisting of a hydrogen atom, a halogeno group, a hydroxyl group, a nitro group, an amino group, an alkyl group having 1 to 6 carbon atoms which may have a substituent(s), an alkoxy group having 1 to 6 carbon atoms which may have a substituent(s) and a mono- or di-alkylamino group having 1 to 6 carbon atoms which may have a substituent(s); $R_2$ is selected from the group consisting of a nitro group, a sulfonic acid group,

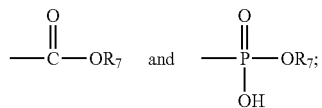

$R_6$ and $R_7$ each independently represent a hydrogen atom or an alkyl group having 1 to 6 carbon atoms which may have a substituent(s); and X represents a methylene group or an oxygen atom,
provided that the following compound is excluded:
a compound wherein X is a methylene group, $R_2$ is

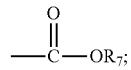

each of $R_1$ and $R_3$-$R_6$ is a hydrogen atom, and $R_7$ is a hydrogen atom or a methyl group.

Further, the present invention provides a CaSR agonistic agent, a kokumi-imparting agent or a therapeutic or preventive agent for diarrhea each comprising a glutamic acid derivative of the following formula (I) or pharmaceutically acceptable salts thereof:

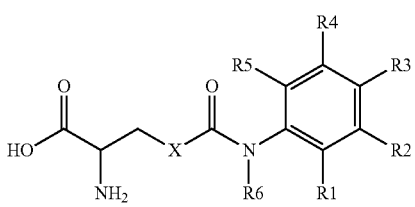

wherein $R_1$-$R_5$ are each independently selected from the group consisting of a hydrogen atom, a halogeno group, a hydroxyl group, a nitro group, an amino group, an alkyl group having 1 to 6 carbon atoms which may have a substituent(s), an alkoxy group having 1 to 6 carbon atoms which may have a substituent(s), a mono- or di-alkylamino group having 1 to 6 carbon atoms which may have a substituent(s), a sulfonic acid group,

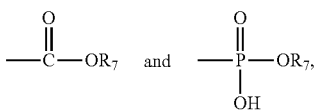

provided that any one of $R_1$-$R_3$ is selected from the group consisting of a nitro group, a sulfonic acid group,

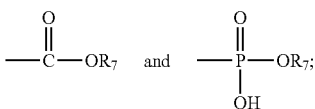

$R_6$ and $R_7$ each independently represent a hydrogen atom, a hydroxyl group or an alkyl group having 1 to 6 carbon atoms which may have a substituent(s); and X represents a methylene group or an oxygen atom.

The present invention also provides a CaSR agonistic agent, a kokumi-imparting agent or a therapeutic or preventive agent for diarrhea each comprising a glutamic acid derivative of the following formula (I) or pharmaceutically acceptable salts thereof:

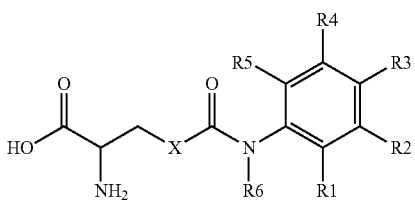

wherein $R_1$ and $R_3$-$R_5$ are each independently selected from the group consisting of a hydrogen atom, a halogeno group, a hydroxyl group, a nitro group, an amino group, an alkyl group having 1 to 6 carbon atoms which may have a substituent(s), an alkoxy group having 1 to 6 carbon atoms which may have a substituent(s) and a mono- or di-alkylamino group having 1 to 6 carbon atoms which may have a substituent(s); $R_2$ is selected from the group consisting of a nitro group, a sulfonic acid group,

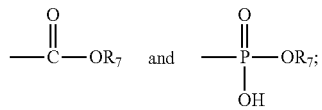

$R_6$ and $R_7$ each independently represent a hydrogen atom or an alkyl group having 1 to 6 carbon atoms which may have a substituent(s); and X represents a methylene group or an oxygen atom.

Effects of the Present Invention

According to the present invention, it becomes possible to provide various compounds having an excellent CaSR agonistic activity, and CaSR agonistic agents, pharmaceutical compositions, preventive or therapeutic agents for diarrhea and kokumi-imparting agents each of which comprise the compound(s).

BEST MODE FOR CARRYING OUT THE INVENTION

Figure 1:
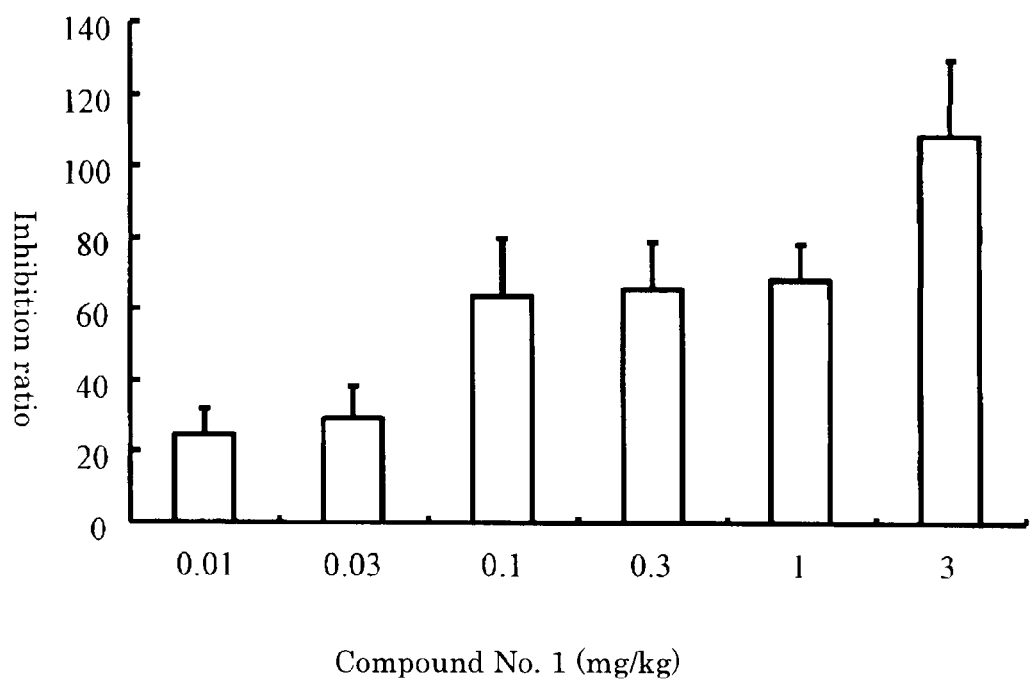
FIG. 1 shows a diagram of the prophylactic activity of Compound No. 1 on diarrhea.

In the glutamic acid derivative of the above formula (I) of the present invention, it is preferable that $R_1$ and $R_3$-$R_5$ are each independently selected from the group consisting of a hydrogen atom, a halogeno group, a hydroxyl group, a nitro group, an amino group, an alkyl group having 1 to 3 carbon atoms which may have a substituent(s), an alkoxy group having 1 to 3 carbon atoms which may have a substituent(s) and a mono- or di-alkylamino group having 1 to 3 carbon atoms which may have a substituent(s). It is more preferable that $R_1$ and $R_3$-$R_5$ are each independently selected from the group consisting of a hydrogen atom, a chloro or bromo group, a hydroxyl group, a nitro group, an amino group, a methyl group and a methoxy group.

In the above formula (I) of the present invention, $R_2$ is preferably a sulfonic acid group, a carboxylic acid group or a phosphonic acid group.

Alternatively, either one of $R_1$ or $R_3$ may be a sulfonic acid group, and $R_4$ is preferably a halogeno group at that time.

In the above formula (I) of the present invention, X is preferably a methylene group.

In the glutamic acid derivative of the above formula (I) or pharmaceutically acceptable salts thereof, any one of $R_1$-$R_3$ is preferably a sulfonic acid group, a carboxylic acid group or a phosphonic acid group.

Among them, $R_2$ is preferably a sulfonic acid group, a carboxylic acid group or a phosphonic acid group, and particularly preferably a sulfonic acid group.

Particularly, in the above formula (I), when $R_2$ is a sulfonic acid group, it is preferable that $R_1$ is a hydrogen atom or a hydroxyl group; $R_3$ is a hydrogen atom, a chloro group, a hydroxyl group, a methyl group or a methoxy group; $R_4$ is a hydrogen atom, a chloro group or a nitro group; $R_5$ is a hydrogen atom, a hydroxyl group, a methyl group or a methoxy group; $R_6$ is a hydrogen atom or a methyl group; and X is a methylene group or an oxygen atom. In the above formula (I), when $R_2$ is a sulfonic acid group, it is most preferable that $R_1$ is a hydrogen atom or a hydroxyl group; $R_3$ is a hydrogen atom, a chloro group or a methyl group; $R_4$ is a hydrogen atom or a chloro group; $R_5$ is a hydrogen atom, a hydroxyl group or a methyl group; $R_6$ is a hydrogen atom; and X is a methylene group.

In the glutamic acid derivative of the above formula (I) or pharmaceutically acceptable salts thereof, particularly when $R_2$ is a carboxylic acid group, it is most preferable that $R_1$ is a hydrogen atom or a hydroxyl group; $R_3$ is a hydrogen atom; $R_4$ is a hydrogen atom or a bromo group; $R_5$ is a hydrogen atom; $R_6$ is a hydrogen atom; and X is a methylene group.

In the glutamic acid derivative of the above formula (I) or pharmaceutically acceptable salts thereof, particularly when $R_2$ is $-PO(OCH_3)OH$ or $-PO(OH)_2$, it is most preferable that $R_1$ is a hydrogen atom; $R_3$ is a hydrogen atom; $R_4$ is a hydrogen atom; $R_5$ is a hydrogen atom; $R_6$ is a hydrogen atom; and X is a methylene group.

In the glutamic acid derivative of the above formula (I) or pharmaceutically acceptable salts thereof, particularly when $R_2$ is a nitro group, it is most preferable that $R_1$ is a hydrogen atom; $R_3$ is a hydrogen atom; $R_4$ is a hydrogen atom; $R_5$ is a hydrogen atom; $R_6$ is a hydrogen atom; and X is a methylene group.

The glutamic acid derivative of the above formula (I) is preferably compounds mentioned in Examples. Among them, Compounds 1, 7, 10, 21, 22, 24, 32, 33, 34, 35 and 37 are preferable among them. Particularly, Compounds 7, 10, 21, 22, 24, 32, 33, 34, 35 and 37 are preferable.

Each of an alkyl group, an alkoxy group and a mono- or di-alkylamino group in the above formula (I) may have a substituent(s). Examples of a substituent include halogens, a hydroxyl group, an alkoxy group, an amino group, a mono- or di-alkylamino group, a carboxyl group and a sulfonic acid group, but it is not limited to those. Further, an alkoxy group and a mono- or di-alkylamino group as the substituent is preferably a lower alkoxy group and a lower mono- or di-alkylamino group, respectively. "Lower" means that a number of carbons in all substituents are 1 to 3.

In the present invention, marketed products can be used as the glutamic acid derivative of the above formula (I) or pharmaceutically acceptable salts thereof. The glutamic acid derivative or pharmaceutically acceptable salts thereof can also be obtained by preferable publicly-known method such as (1) chemical synthesis and (2) synthesis by enzyme reaction. In the present invention, it is easy to use the method of chemically synthesizing the glutamic acid derivative of the above formula (I) or pharmaceutically acceptable salts thereof as mentioned in Examples. Examples of the chemical synthesis include liquid-phase synthesis and solid-phase synthesis.

The synthesized glutamic acid derivative can be purified with the ordinary method such as ion-exchange chromatography, reversed-phase high-performance liquid chromatography, affinity chromatography and recrystallization. The above chemical synthesis and subsequent purification are well known in this technical field.

The glutamic acid derivative of the above formula (I) of the present invention may be in the form of pharmaceutically acceptable salts thereof. Examples of the pharmaceutically acceptable salts of the glutamic acid derivative of the above formula (I) of the present invention include edible salts. For example, to acidic groups such as a carboxyl group and a sulfonic acid group in the formula (I), the salts include ammonium salts; salts with alkali metals such as sodium and potassium; salts with alkaline earth metals such as calcium and magnesium; aluminum salts; zinc salts; salts with organic amines such as triethylamine, ethanolamine, morpholine, pyrrolidine, piperidine, piperazine and dicyclohexylamine; and salts with basic amino acids such as arginine and lysine. When a basic group(s) exists in the formula (I), to such basic groups, the salts include salts with inorganic acids such as a hydrochloric acid, a sulfuric acid, a phosphoric acid, a nitric acid and a hydrobromic acid; salts with organic carboxylic acids such as an acetic acid, a citric acid, a benzoic acid, a maleic acid, a fumaric acid, a tartaric acid, a succinic acid, a tannic acid, a butyric acid, a hibenzic acid, a pamoic acid, an enanthic acid, a decanoic acid, a teoclate, a salicylic acid, a lactic acid, an oxalic acid, a mandelic acid and a malic acid; and salts with organic sulfonic acids such as a methane sulfonic acid, a benzene sulfonic acid and a p-toluene sulfonic acid.

In the specification, "CaSR" indicates a calcium sensing receptor, and it belongs to the class C of seven transmembrane receptors. It is also called a calcium receptor. A "CaSR agonist" indicates a compound bonding to CaSR and activating CaSR. A "CaSR agonistic agent" indicates an agent or a substance bonding to CaSR and activating CaSR. Further, "activating CaSR" indicates that a ligand bonds to CaSR and thereby activates guanine nucleotide-binding proteins to transmit signals. The behavior that a compound bonds to CaSR and activates CaSR is called "CaSR agonistic activity".

The method for screening for a compound having CaSR agonistic activity are specifically illustrated as follows, but it is not limited to these steps.

1) Add a tested substance to CaSR activity measurement system for measuring CaSR activity and measure the CaSR activity thereof.

2) Compare the CaSR activity when adding a tested substance and the CaSR activity without adding it.

3) Select a tested substance that CaSR agonistic activity is shown when adding the tested substance.

The measurement of CaSR activity can be conducted by the measurement system with cells expressing CaSR, for example. The cells may be those internally expressing CaSR or recombinant cells externally introducing CaSR genes. Any CaSR activity measurement system is usable without limitation, provided that, when adding a CaSR-specific extracellular ligand (an activating substance) to the cells expressing CaSR, the system can detect the binding (reaction) of the activating substance to CaSR or it can transmit detectable signals in the cells in response to the binding (reaction) of the activating substance to CaSR. When CaSR activity is detected by the reaction with a tested substance, it is determined that the tested substance has CaSR stimulating activity.

A preferable example of CaSR includes human CaSR encoded by the human CaSR gene which is registered as GenBank Accession No. NM_000388. Meanwhile, CaSR is not limited to the protein encoded by the gene of the above sequence. Insofar as proteins having CaSR function are encoded, the proteins may be those encoded by the gene sharing 60% or more, preferably 80% or more, and more preferably 90% or more of homology with the above sequence. The CaSR function can be examined by expressing the above genes in cells and measuring changes of current and changes of intracellular calcium ion concentration in calcium addition.

The origin of CaSR is not particularly limited, and in addition to the human CaSR, examples thereof include any animal-derived CaSR such as those of mouse, rat and canine.

As mentioned above, CaSR activity can be confirmed by using living cells expressing CaSR or fragments thereof; cell membranes expressing CaSR or fragments thereof; the in vitro system containing proteins of CaSR fragments thereof.

The measurement of CaSR activity with living cells is illustrated below as one example, but it is not limited to the following.

CaSR is expressed in culture cells such as *Xenopus* oocytes, hamster ovary cells and human embryonic kidney cells. The expression becomes possible by cloning a CaSR gene to a plasmid having a foreign gene; and then introducing cRNA of the plasmid or cRNA generated from the plasmid template. The electrophysiological method, a fluorescent indicating reagent for detecting increase of intracellular calcium, or the like can be used for detecting the reaction.

The expression of CaSR is first confirmed by a response by calcium or a specifically activating agent.

An oocyte wherein the intracellular current was observed or a culture cell wherein fluorescence of a fluorescent indicating reagent was observed is used to calcium of around 5 mM concentration. The concentration of calcium is changed, and concentration dependence thereof is measured. Next, a tested substance is prepared to become 1 µM to 1 mM, and added to an oocyte or a culture cell. Then, CaSR activity thereof in the presence of the tested substance is measured to measure CaSR agonistic activity of the tested substance.

The CaSR agonistic agent can comprise any glutamic acid derivative or pharmaceutically acceptable salts thereof included in a glutamic acid derivative of the above formula (I) alone or in combinations with preferable two or more kinds thereof. Further, the agent can comprise any solid or liquid carrier or additives each of which is pharmaceutically, physiologically and experimentally acceptable and also acceptable as a food product.

Examples of the carrier include glucose, lactose, sucrose, starch, mannitol, dextrin, glycerides of fatty acids, polyethylene glycols, hydroxyethyl starch, ethylene glycols, polyoxyethylene sorbitan fatty acid ester, gelatin, albumin, amino acids, water and a normal saline solution. If necessary, common additives such as stabilizing agents, moisturizing agents, emulsifying agents, binders and tonicity agents can be preferably added to the CaSR agonistic agent of the present invention.

The above additives are not particularly limited as long as they are usually used for purposes corresponding to the purposes. Examples of the additives include flavoring agents, sugars, sweetening agents, dietary fibers, vitamins, amino acids such as a monosodium glutamate (MSG), nucleic acids such as an inosine monophosphate (IMP), inorganic salts such as sodium chloride and water.

The CaSR agonistic agent of the present invention can be used in any form without limitation of properties, such as dry powder, paste and a solution. Further, the CaSR agonistic agent of the present invention can be used in medical drugs, quasi drugs, food products, reagents, or the like.

The usage amount of the CaSR agonistic agent of the present invention can be preferably adjusted corresponding to purposes. For example, in the case of orally administering the agent to a target, a total amount of a glutamic acid derivative of the formula (I) or pharmaceutically acceptable salts thereof is preferably 0.01 to 10 g per 1 kg of body weight in one administration, and more preferably 0.1 to 1 g.

The frequency of administration is not particularly limited, and the agent can be administered once or several times per day.

In the case of using the CaSR agonistic agent of the present invention in food products or reagents, 0.000001 to 10 g per one prescription is preferable, and 0.00001 to 1 g per one prescription is more preferable.

The content of the glutamic acid derivative of the formula (I) or pharmaceutically acceptable salts thereof in the CaSR agonistic agent of the present invention is not particularly limited only if it fits the usage amount mentioned above. The content thereof is preferably 0.000001 to 99.9999 weight % per dry weight, more preferably 0.00001 to 99.999 weight %, and particularly preferably 0.0001 to 99.99 weight %.

The CaSR agonistic agent of the present invention can further contain one or more kinds of a known substance(s) having CaSR agonistic activity.

Examples of the known substance having CaSR agonistic activity include cations such as calcium and gadolinium; basic peptides such as polyarginine and polylysine; polyamines such as putrescine, spermine and spermidine; proteins such as protamine; amino acids such as phenylalanine; peptides such as glutathione; and analogues of cinacalcet, but it is not limited to those.

Further, in addition to the known substance having CaSR agonistic activity, the CaSR agonistic agent of the present invention can contain any known substance corresponding to purposes.

"Kokumi" in the specification indicates the taste that cannot be expressed with five basic tastes of sweetness, saltiness, sourness, bitterness and umami, and the taste that enhances marginal tastes of the basic tastes, such as thickness, growth (mouthfullness), continuity, and harmony. A "kokumi-imparting agent" indicates an agent or a substance that can enhance at least one of the five basic tastes of sweetness, saltiness, sourness, bitterness and umami, and impart the marginal tastes of the basic tastes such as thickness, growth (mouthfullness), continuity, and harmony. Accordingly, the kokumi-imparting agent of the present invention can be used as a sweet taste enhancing agent, a salty taste enhancing agent, a sour taste enhancing agent, a bitter taste enhancing agent or an umami taste enhancing agent together with improving the quality of taste.

The kokumi-imparting effects can be confirmed by the method such as a gustatory test by a human being as mentioned in Examples of the present invention, but it is not limited to those.

The kokumi-imparting agent of the present invention can comprise any glutamic acid derivative or pharmaceutically acceptable salts thereof included in a glutamic acid derivative of the above formula (I) alone or in combinations with preferable two or more kinds thereof. Further, various other additives can be preferably added to the kokumi-imparting agent.

The above additives can be used without limitation as long as it is known that they can be added or dispensed to foods and beverages such as seasonings, food products and beverages. Examples of the additives include flavoring agents, sugars, sweetening agents, dietary fibers, vitamins, amino acids such as a monosodium glutamate (MSG), nucleic acids such as an inosine monophosphate (IMP), inorganic salts such as sodium chloride and water.

The present invention also provides foods and beverages comprising a glutamic acid derivative of the above formula (I). The usage amount of the glutamic acid derivative of the above formula (I) of the present invention or pharmaceutically acceptable salts thereof or a kokumi-imparting agent to foods and beverages can be the amount effective at imparting kokumi and preferably adjusted depending on the use thereof. For example, in the case of using it in seasonings, food products or beverages, a total amount of a glutamic acid derivative of the above formula (I) of the present invention or pharmaceutically acceptable salts thereof or a kokumi-imparting agent is 1 ppb weight to 99.9 weight % in a seasoning, food or beverage, and more preferably 10 ppb weight to 99.9 weight %.

Accordingly, it is possible to produce kokumi-imparted foods and beverages by adding one or more kinds of a glutamic acid derivative of the above formula (I) of the present invention or pharmaceutically acceptable salts thereof or a kokumi-imparting agent to a food or a beverage so that 1 ppb weight to 99.9 weight %, and preferably 10 ppb weight to 99.9 weight % thereof can be contained in the food or the beverage.

Further, it is also possible to produce kokumi-imparted foods and beverages by adding a kokumi-imparted seasoning(s) which comprises 1 ppb weight to 99.9 weight % of one or more kinds of a glutamic acid derivative of the above formula (I) of the present invention or pharmaceutically acceptable salts thereof to a food or a beverage so that 0.01 to 10 weight %, and preferably 0.1 to 10 weight % of the seasoning(s) can be contained in the food or the beverage.

The kokumi-imparting agent of the present invention can further contain one or more kinds of a known substance(s) having CaSR agonistic activity.

Examples of the known substance having CaSR agonistic activity include cations such as calcium and gadolinium; basic peptides such as polyarginine and polylysine; polyamines such as putrescine, spermine and spermidine; proteins such as protamine; amino acids such as phenylalanine; peptides such as glutathione; and analogues of cinacalcet, but it is not limited to those.

Further, in addition to the known substance having CaSR agonistic activity, the kokumi-imparting agent of the present invention can contain any known substance corresponding to purposes.

When adding a glutamic acid derivative of the above formula (I) of the present invention or pharmaceutically acceptable salts thereof or a kokumi-imparting agent to foods and beverages, any form thereof can be used without limitation of properties, such as dry powder, paste and a solution.

The pharmaceutical composition of the present invention can comprise any glutamic acid derivative or pharmaceutically acceptable salts thereof included in a glutamic acid derivative of the above formula (I) alone or in combinations with preferable two or more kinds thereof.

The usage amount of the pharmaceutical composition of the present invention can be preferably adjusted corresponding to purposes. For example, in the case of orally administering the pharmaceutical composition to a target, a total amount of a glutamic acid derivative of the formula (I) or pharmaceutically acceptable salts thereof is preferably 0.01 to 10 g per 1 kg of body weight in one administration, and more preferably 0.1 to 1 g. The frequency of administration is not particularly limited, and the composition can be administered once or several times per day.

In the case of using the pharmaceutical composition of the present invention in food products or reagents, 0.001 to 10 g per one prescription is preferable, and 0.01 to 1 g per one prescription is more preferable.

The content of the glutamic acid derivative of the formula (I) or pharmaceutically acceptable salts thereof in the pharmaceutical composition of the present invention is not particularly limited only if it fits the usage amount mentioned above. The content thereof is preferably 0.000001 to 99.9999 weight % per dry weight, more preferably 0.00001 to 99.999 weight %, and particularly preferably 0.0001 to 99.99 weight %.

The pharmaceutical composition of the present invention can further contain one or more kinds of a known substance(s) having CaSR agonistic activity.

Examples of the known substance having CaSR agonistic activity include cations such as calcium and gadolinium; basic peptides such as polyarginine and polylysine; polyamines such as putrescine, spermine and spermidine; proteins such as protamine; amino acids such as phenylalanine; peptides such as glutathione; and analogues of cinacalcet, but it is not limited to those.

Further, in addition to the known substance having CaSR agonistic activity, the pharmaceutical composition of the present invention can contain any known substance corresponding to purposes.

The method of applying the pharmaceutical composition of the present invention is not particularly limited, and any invasive or non-invasive administration such as oral administration and injection is applicable. Suppository or transdermal administration is also applicable. It is possible to administer an active ingredient by formulating it into a common pharmaceutical preparation form together with a solid or liquid pharmaceutical carrier that is suitable for the administration method such as oral administration and injection. Examples of the preparation form include solid agents such as tablets, granules, powders and capsules; liquid agents such as solutions, suspensions and emulsifying agents; and freeze-drying agents. These preparations can be prepared by common maneuver in pharmaceutical preparations. Further, any solid or liquid carrier or additives each of which is pharmaceutically and physiologically acceptable can be added to the pharmaceutical composition of the present invention.

Examples of the carrier include glucose, lactose, sucrose, starch, mannitol, dextrin, glycerides of fatty acids, polyethylene glycols, hydroxyethyl starch, ethylene glycols, polyoxyethylene sorbitan fatty acid ester, gelatin, albumin, amino acids, water and a normal saline solution. If necessary, common additives such as stabilizing agents, moisturizing agents, emulsifying agents, binders and tonicity agents can be preferably added to the pharmaceutical composition of the present invention.

In the specification, diarrhea includes all kinds of diarrhea such as irritable colon syndrome, functional diarrhea, inflammatory bowel disease, diverticulitis, bacterial diarrhea and dyspepsia.

The therapeutic or preventive agent for diarrhea of the present invention can comprise any glutamic acid derivative or pharmaceutically acceptable salts thereof included in a glutamic acid derivative of the above formula (I) alone or in combinations with preferable two or more kinds thereof.

The usage amount of the therapeutic or preventive agent for diarrhea of the present invention can be preferably adjusted corresponding to purposes. For example, in the case of orally administering the agent to a target, a total amount of a glutamic acid derivative of the formula (I) or pharmaceutically acceptable salts thereof is preferably 0.01 to 10 g per 1 kg of body weight in one administration, and more preferably 0.1 to 1 g. The frequency of administration is not particularly limited, and the agent can be administered once or several times per day.

In the case of using the therapeutic or preventive agent for diarrhea of the present invention in food products or reagents, 0.001 to 10 g per one prescription is preferable, and 0.01 to 1 g per one prescription is more preferable.

The content of the glutamic acid derivative of the formula (I) or pharmaceutically acceptable salts thereof in the therapeutic or preventive agent for diarrhea of the present invention is not particularly limited only if it fits the usage amount mentioned above. The content thereof is preferably 0.000001 to 99.9999 weight % per dry weight, more preferably 0.00001 to 99.999 weight %, and particularly preferably 0.0001 to 99.99 weight %.

The therapeutic or preventive agent for diarrhea of the present invention can further contain one or more kinds of a known substance(s) having CaSR agonistic activity.

Examples of the known substance having CaSR agonistic activity include cations such as calcium and gadolinium; basic peptides such as polyarginine and polylysine; polyamines such as putrescine, spermine and spermidine; proteins such as protamine; amino acids such as phenylalanine; peptides such as glutathione; and analogues of cinacalcet, but it is not limited to those.

Further, in addition to the known substance having CaSR agonistic activity, the therapeutic or preventive agent for diarrhea of the present invention can contain any known substance corresponding to purposes.

The method of applying the therapeutic or preventive agent for diarrhea of the present invention is not particularly limited, and any invasive or non-invasive administration such as oral administration and injection is applicable. Suppository or transdermal administration is also applicable. It is possible to administer an active ingredient by formulating it into a common pharmaceutical preparation form together with a solid or liquid pharmaceutical carrier that is suitable for the administration method such as oral administration and injection. Examples of the preparation form include solid agents such as tablets, granules, powders and capsules; liquid agents such as solutions, suspensions and emulsifying agents; and freeze-drying agents. These preparations can be prepared by common maneuver in pharmaceutical preparations. Further, any solid or liquid carrier or additives each of which is pharmaceutically and physiologically acceptable can be added to the therapeutic or preventive agent for diarrhea of the present invention.

Examples of the carrier include glucose, lactose, sucrose, starch, mannitol, dextrin, glycerides of fatty acids, polyethylene glycols, hydroxyethyl starch, ethylene glycols, polyoxyethylene sorbitan fatty acid ester, gelatin, albumin, amino acids, water and a normal saline solution. If necessary, common additives such as stabilizing agents, moisturizing agents, emulsifying agents, binders and tonicity agents can be preferably added to the therapeutic or preventive agent for diarrhea of the present invention.

The CaSR agonistic agent, kokumi-imparting agent, and therapeutic or preventive agent for diarrhea of the present invention can be used as foods and beverages or supplements wherein each agent has each effect. For example, it is possible to prepare foods and beverages indicating on the container or package thereof that it has a therapeutic or preventive effect on diarrhea. The form of the foods and beverages is not particularly limited, and the foods and beverages can be produced by the same production method as that of usual food products, using the same materials used in producing such food products, except that a compound(s) having CaSR agonistic activity is dispensed. Examples of food products include seasonings; beverages such as juice and milk; confectionery; jellies; health foods; processed agricultural products; processed animal products such as milk and cheese; and food supplements.

(Representative Method of Synthesizing a Glutamic Acid Derivative of the Formula (I))

The representative method of producing the compound of the present invention is illustrated below.

In the following production method, it is production-technologically effective in some kinds of functional groups that the functional group is substituted with a preferable protective group, i.e. a group that can be easily converted into the functional group during the functional group is in a raw material or intermediate. After that, the protective group is removed if necessary to obtain the intended compound. Examples of the functional group include an amino group, a hydroxyl group and a carboxyl group. Further, examples of the protective group thereof include t-butoxycarbonyl (Boc), benzyloxycarbonyl (Z or Cbz) and 9-fluorenylmethoxycarbonyl (Fmoc) as a protective group of an amino group; t-butyl (tBu) and benzyl (Bn or Bzl) as a protective group of a carboxyl group; and protective groups described on the third edition of Protective Groups in Organic Synthesis (T. W. Green and P. G. M. Wuts, JOHN WILLY & SONS, INC.) They can be preferably used corresponding to the reaction conditions. The introduction and deprotection of a protective group can be conducted at the right time in accordance with the method described on the above referential literature. For example, functional groups represented as Prot1 and Prot2 in the following production methods 1 and 2 indicate that they are used as protective groups, but functional groups are not limited to those.

(Production method 1)

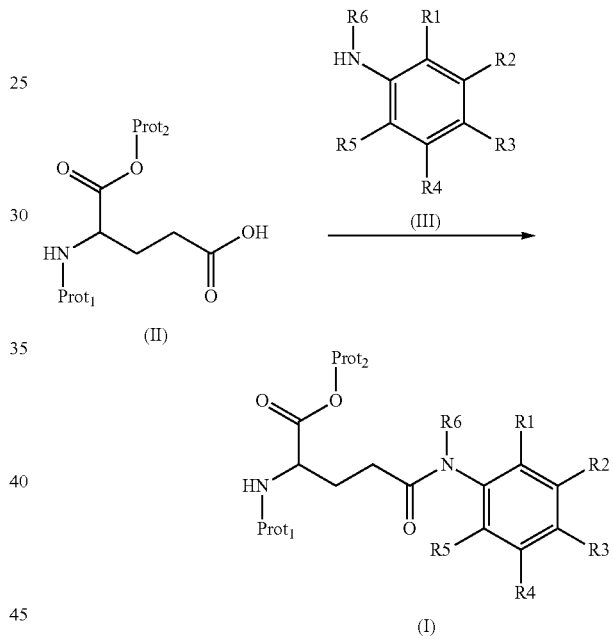

The production method 1 is a reaction comprising the step of conducting a condensation reaction of a carboxylic acid and an amine with a compound (II) and a compound (III) to obtain a compound (I).

This reaction can be conducted in accordance with the ordinary method wherein a compound (II) and an amine derivative (III) are used equivalently or one of them is used excessively in the presence of a condensation agent. Preferable examples of a condensation agent include N,N-dicyclohexylcarbodiimide (DCC), 1-ethyl-3-[3-(N,N-dimethylamino)propyl]carbodiimide (EDCI or WSC), O-benzotriazole-1-yl-N,N,N',N'-tetramethyluronium hexafluorophosphate (HBTU), carbonyldiimidazole (CDI), 4-(4,6-dimethoxy-1,3,5-triazin-2-yl) 4-methylmorphonium chloride (DMTMM), and 2-(7-azabenzotriazole-1-yl)-N,N,N',N'-tetramethyluronium hexafluorophosphate (HATU). These condensation agents are used equivalently or excessively to a carboxylic acid. As for a solvent, those that are not involved in the reaction can be used. Examples of a solvent include N,N-dimethylformamide (DMF), dioxane, water, methanol, ethanol, tetrahydrofuran (THF), dichloromethane, dichloroethane, diethylether, chloroform, dimethoxyethane (DME), ethyl acetate, toluene, acetonitrile, dimethylsulfoxide (DMSO), and a mixed solvent thereof. It is preferable to preferably select a solvent depending on a raw material, the kind of a condensation agent, and the like. The reaction can smoothly proceed in the presence of a base such as triethylamine, diisopropylethylamine, N-methylmorpholine, pyridine and 4-dimethylaminopyridine; or by reacting said base(s) as a solvent. Though the reaction is usually conducted at cooling or room temperature, it is sometime preferable that the reaction is conducted under heating depending on the conditions of the condensation reaction.

Further, the compound (I) can be produced by the method comprising the steps of introducing a carboxylic acid into an active derivative, and condensing it with an amine. In this case, the compound (II) and the amine derivative (III) are used equivalently or one of them is used excessively. Examples of an active derivative of a carboxylic acid include phenol compounds such as p-nitrophenol; active esters obtained by reacting N-hydroxyamine compounds such as 1-hydroxysuccinimide (HOSu), 1-hydroxybenzotriazole (HOBt) and 7-aza-1-hydroxybenzotriazole (HOAt); mixed acid anhydrides obtained by reacting monoalkyl carbonate and an organic acid; phosphoric mixed acid anhydrides obtained by reacting diphenylphosphoryl chloride and N-methylmorpholine; acid azides obtained by reacting an ester with hydrazine and an alkyl nitrite successively; acid halides such as acid chlorides and acid fluorides; and symmetrical acid anhydrides.

When synthesizing an active derivative of a carboxylic acid, an activating reagent is used equivalently or excessively to the compound (II). Other than said reaction conditions, any reaction can be used provided that it is a reaction that an amide binding is formed.

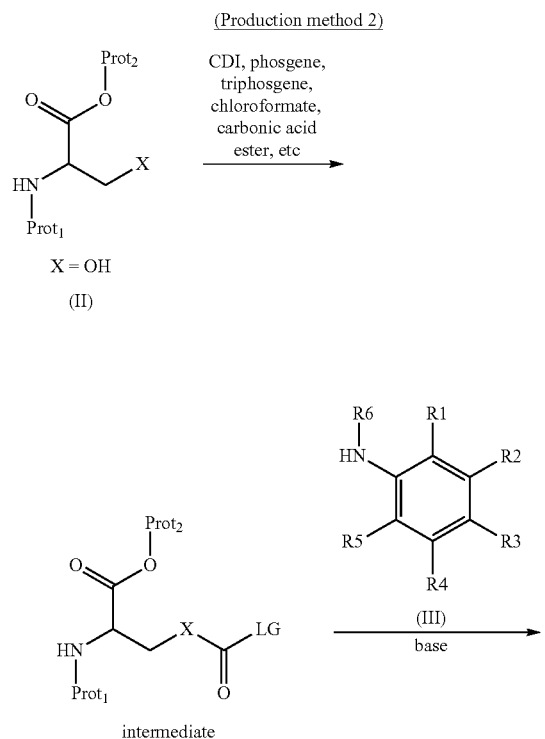

(Production method 2)

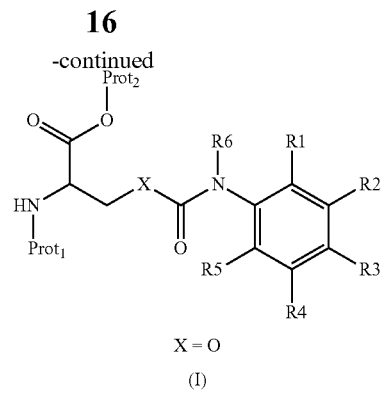

$X = O$ (I)

The production method 2 is a reaction comprising the steps of obtaining an intermediate from a compound (IIa) and acting a compound (III) on the obtained intermediate to obtain a compound (I).

In the reaction, an intermediate can be obtained by acting a compound (IIa) with an equivalent or a little excessive reagent such as N,N-carbonyldiimidazole, phosgene, triphosgene, benzyl chloroformate and methyl carbonate. At that time, it is preferable to conduct the reaction using a solvent that is not involved in the reaction, e.g., N,N-dimethylformamide (DMF), dioxane, tetrahydrofuran (THF), dichloromethane, dichloroethane, diethylether, chloroform, dimethoxyethane (DME), ethyl acetate, toluene, acetonitrile, dimethylsulfoxide (DMSO), and a mixed solvent thereof. Though the reaction is usually conducted at cooling or room temperature, it is sometime preferable that the reaction is conducted under heating depending on the kinds of a reagent and a compound. The obtained intermediate is, if necessary, substituted to a preferable solvent, and the reaction is conducted using the intermediate and the compound (III) equivalently or using one of them a little excessively. In the reaction, it is possible to make an organic base such as triethylamine or an inorganic base such as potassium carbonate coexist. Though the reaction is usually conducted under cooling to under heating of around 100° C., it is sometime preferable to conduct the reaction under further heating depending on the kind of a compound. Other than the above method, any reaction can be used provided that it is a reaction that a carbamate is formed.

(Production Method 3)

Thus produced compound of the present invention can be used as a free compound as itself, or can be isolated or purified as salts thereof with common chemical operations such as extraction, precipitation, fractional chromatography, fractional crystallization and recrystallization. The salts of the compound can be produced by conducting a general salt-forming reaction to the free compound of the present invention.

Further, when the compound of the present invention has asymmetric carbons, optical isomers exist. The optical isomers can be produced by the method comprising the steps of introducing the compound into a diastereomeric salt with an optically active acid or base, and fractionally-crystallizing it; the optical resolution method with the ordinary method such as column chromatography; or the synthesis method with an optically active raw compound.

EXAMPLES

Next, Examples will further illustrate the present invention. They only explain the present invention and do not particularly limit the invention.

In the specification, the ordinary method indicates the method generally used as a chemical operation such as liquid separation, drying, filtration and concentration.

In the specification, a purification process A indicates the method comprising the steps of putting a crude substance obtained by the ordinary method in a reverse-phase high-performance liquid chromatography using octadecylsilyl silica gel as a filler, eluting it with a mixed solution of water and acetonitrile that contains a 0.1% (v/v) trifluoroacetic acid, and concentrating and freeze-drying an intended fraction.

The following examples will further illustrate synthesis of the representative compounds of the present invention shown in Table 1. They only explain the compounds of the present invention and do not particularly limit them.

TABLE 1

(I)

| Comp. No. | $R_1$ | $R_2$ | $R_3$ | $R_4$ | $R_5$ | $R_6$ | X |
|---|---|---|---|---|---|---|---|
| 1 | H | $SO_3H$ | H | H | H | H | $CH_2$ |
| 2 | H | $SO_3H$ | OMe | H | H | H | $CH_2$ |
| 3 | H | $SO_3H$ | H | H | OMe | H | $CH_2$ |
| 4 | H | $SO_3H$ | Me | H | Me | H | $CH_2$ |
| 5 | H | $SO_3H$ | Me | H | H | H | $CH_2$ |
| 6 | H | $SO_3H$ | H | $NO_2$ | OH | H | $CH_2$ |
| 7 | OH | $SO_3H$ | H | Cl | H | H | $CH_2$ |
| 8 | H | $SO_3H$ | H | H | OH | H | $CH_2$ |
| 9 | H | $SO_3H$ | Cl | H | H | H | $CH_2$ |
| 10 | OH | $SO_3H$ | H | H | H | H | $CH_2$ |
| 11 | H | $SO_3H$ | OH | H | H | H | $CH_2$ |
| 12 | H | $SO_3H$ | H | H | H | $CH_3$ | $CH_2$ |
| 13 | H | $SO_3H$ | H | H | H | H | O |
| 14 | H | $CO_2H$ | H | H | H | H | $CH_2$ |
| 15 | OH | $CO_2H$ | H | H | H | H | $CH_2$ |
| 16 | H | $CO_2H$ | H | Br | H | H | $CH_2$ |
| 17 | H | PO(OMe)OH | H | H | H | H | $CH_2$ |
| 18 | H | $PO(OH)_2$ | H | H | H | H | $CH_2$ |
| 19 | H | $NO_2$ | H | H | H | H | $CH_2$ |
| 20 | H | H | H | H | H | H | $CH_2$ |

Example I

Synthetic Example 1

Synthesis of $N^5$-(3-sulfophenyl)-L-glutamine (Compound No. 1)

Boc-Glu-OtBu (75 mg, 0.247 mmol), HATU (112 mg, 0.296 mmol) and HOAt (41 mg, 0.296 mmol) were dissolved in 1 mL of DMF. Triethylamine (52 μL) was added thereto and stirred at room temperature for 10 minutes. 3-Sulfoaniline (43 mg, 0.247 mmol) was added thereto and stirred overnight at room temperature. After removing a solvent, purification was conducted in accordance with the purification process A. The obtained intermediate was dissolved in 2 mL of a trifluoroacetic acid and stirred at room temperature for 3 hours, and a solvent was removed therefrom. The obtained product was purified in accordance with the purification process A to obtain a title compound.

Yield amount: 30.8 mg (0.10 mmol) yield: 41%

1H-NMR (D2O, 300 MHz): δ 7.89 (s, 1H), 7.67-7.62 (m, 2H), 7.58-7.53 (m, 1H), 3.99 (t, 1H, J=6.4 Hz), 2.73-2.66 (m, 2H), 2.33-2.25 (m, 2H)

ESI (m/z): 303 [M+H]+, 301 [M−H]−

Synthetic Example 2

Synthesis of $N^5$-(4-methoxy-3-sulfophenyl)-L-glutamine (Compound No. 2)

A title compound was obtained by the same method as that of the synthetic example 1 except that p-anisidine-3-sulfonic acid was used instead of 3-sulfoaniline.

Yield amount: 24.7 mg yield: 23%

1H-NMR (D2O, 300 MHz): δ 7.96 (s, 1H), 7.53 (d, 1H), 7.04 (d, 1H), 3.98 (t, 1H), 3.78 (s, 3H), 2.63-2.52 (m, 2H), 2.30-2.05 (m, 2H)

ESI (m/z): 333 [M+H]+

Synthetic Example 3

Synthesis of $N^5$-(2-methoxy-5-sulfophenyl)-L-glutamine (Compound No. 3)

A title compound was obtained by the same method as that of the synthetic example 1 except that o-anisidine-5-sulfonic acid was used instead of 3-sulfoaniline.

Yield amount: 75.7 mg yield: 69%

1H-NMR (D2O, 300 MHz): δ 7.65 (s, 1H), 7.45 (d, 1H), 7.04 (d, 1H), 3.96 (t, 1H), 3.79 (s, 3H), 2.80-2.50 (m, 2H), 2.25-2.10 (m, 2H)

ESI (m/z): 333 [M+H]+

Synthetic Example 4

Synthesis of $N^5$-(2,4-dimethyl-5-sulfophenyl)-L-glutamine (Compound No. 4)

A title compound was obtained by the same method as that of the synthetic example 1 except that 2,4-dimethylaniline-5-sulfonic acid sodium salt was used instead of 3-sulfoaniline.

Yield amount: 70.3 mg yield: 64%

1H-NMR (D2O, 300 MHz): δ 7.55 (s, 1H), 7.17 (s, 1H), 3.97 (t, 1H), 2.67-2.55 (m, 2H), 2.43 (s, 3H), 2.30-2.15 (m, 2H), 2.08 (s, 3H)

ESI (m/z): 331 [M+H]+

Synthetic Example 5

Synthesis of $N^5$-(4-methyl-3-sulfophenyl)-L-glutamine (Compound No. 5)

A title compound was obtained by the same method as that of the synthetic example 1 except that 5-amino-2-methylbenzene-1-sulfonic acid was used instead of 3-sulfoaniline.

Yield amount: 79.3 mg yield: 76%

1H-NMR (D2O, 300 MHz): δ 7.76 (s, 1H), 7.34 (d, 1H), 7.24 (d, 1H), 3.93 (t, 1H), 2.60-2.45 (m, 2H), 2.44 (s, 3H), 2.30-2.00 (m, 2H)

ESI (m/z): 317 [M+H]+

Synthetic Example 6

Synthesis of $N^5$-(2-hydroxy-3-nitro-5-sulfophenyl)-L-glutamine (Compound No. 6)

A title compound was obtained by the same method as that of the synthetic example 1 except that 3-amino-4-hydroxy-5-nitrobenzene-sulfonic acid was used instead of 3-sulfoaniline.

Yield amount: 73.8 mg yield: 62%
1H-NMR (D2O, 300 MHz): δ 8.37 (s, 1H), 8.24 (s, 1H), 3.94 (t, 1H), 2.64-2.70 (m, 2H), 2.09-2.23 (m, 2H)
ESI (m/z): 364 [M+H]+

Synthetic Example 7

Synthesis of $N^5$-(5-chloro-2-hydroxy-3-sulfophenyl)-L-glutamine (Compound No. 7)

Boc-Glu-OtBu (100 mg, 0.33 mmol) and HOBt hydrate (65.6 mg, 0.43 mmol) were dissolved in 2 mL of DMF, and triethylamine (0.137 mL) was added thereto. After cooling the mixture down to 0° C., diisopropylcarbodiimide (66.4 μL, 0.43 mmol) and 2-amino-4-chlorophenol-6-sulfonic acid (73.7 mg, 0.33 mmol) were added thereto and stirred overnight at room temperature. After removing a solvent, purification was conducted in accordance with the purification process A. The obtained intermediate was dissolved in 2 mL of TFA and stirred at room temperature for 2 hours. 2 mL of methylene chloride was added thereto, and a precipitate was taken by filtration to obtain a title compound.

Yield amount: 16.8 mg yield: 14.4%
1H-NMR (DMSO-d6, 300 MHz): δ 11.07 (s, 1H), 9.39 (s, 1H), 8.20-8.40 (br, 2H), 8.02 (s, 1H), 7.14 (s, 1H), 3.95 (t, 1H, J=6.4 Hz), 2.64 (m, 2H), 2.07 (m, 2H)
ESI (m/z): 353 [M+H]+

Synthetic Example 8

Synthesis of $N^5$-(2-hydroxy-5-sulfophenyl)-L-glutamine (Compound No. 8)

A title compound was obtained by the same method as that of the synthetic example 7 except that 2-aminophenol-4-sulfonic acid was used instead of 2-amino-4-chlorophenol-6-sulfonic acid.

Yield amount: 31.5 mg yield: 30%
1H-NMR (D2O, 300 MHz): δ 7.77 (s, 1H), 7.44 (d, 1H), 6.94 (d, 1H), 4.00-3.85 (m, 1H), 2.65-2.57 (m, 2H), 2.19-2.10 (m, 2H)
ESI (m/z): 319 [M+H]+

Synthetic Example 9

Synthesis of $N^5$-(4-chloro-3-sulfophenyl)-L-glutamine (Compound No. 9)

A title compound was obtained by the same method as that of the synthetic example 7 except that 4-chloroaniline-3-sulfonic acid (68.4 mg) was used instead of 2-amino-4-chlorophenol-6-sulfonic acid.

Yield amount: 47.8 mg yield: 43%
1H-NMR (D2O, 300 MHz): δ 7.91 (s, 1H), 7.50-7.45 (m, 2H), 4.00-3.85 (m, 1H), 2.60-2.40 (m, 2H), 2.25-2.15 (m, 2H)
ESI (m/z): 337 [M+H]+

Synthetic Example 10

Synthesis of $N^5$-(2-hydroxy-3-sulfophenyl)-L-glutamine (Compound No. 10)

Z-Glu-OBn (371 mg, 1 mmol) was dissolved in methylene chloride (1 mL), and CDI (180 mg, 1.1 mmol) was added thereto and stirred at room temperature for 30 minutes. Then, 2-amino-4-chlorophenol-6-sulfonic acid (223 mg, 1 mmol) and THF (1 mL) were added thereto and stirred overnight at room temperature. After removing a solvent, purification was conducted in accordance with the purification process A. The obtained intermediate was dissolved in a mixed solvent of methanol and water. Pd/C in catalyst quantity was added thereto and stirred under hydrogen atmosphere overnight at room temperature. After filtering out the catalyst and removing a solvent, purification was conducted in accordance with the purification process A to obtain a title compound.

Yield amount: 120 mg (0.40 mmol) yield: 40%
1H-NMR (D2O, 300 MHz): δ 7.67 (d, 1H, J=7.9 Hz), 7.62 (d, 1H, J=8.2 Hz), 7.07 (dd, 1H, J=7.9 Hz, 8.2 Hz), 3.92-3.97 (m, 1H), 2.59-2.64 (m, 2H), 2.25-2.20 (m, 2H)
ESI (m/z): 303 [M+H]+

Synthetic Example 11

Synthesis of $N^5$-(4-hydroxy-3-sulfophenyl)-L-glutamine (Compound No. 11)

Boc-Glu-OtBu (100 mg, 0.33 mmol) was dissolved in methylene chloride (1 mL) and THF (1 mL). CDI (65 mg, 1.1 mmol) was added thereto and stirred at room temperature for 30 minutes. Then, 5-amino-2-hydroxybenzene sulfonic acid salt (77 mg, 0.33 mmol) was added thereto and stirred overnight at room temperature. After removing a solvent, purification was conducted in accordance with the purification process A. The obtained intermediate was dissolved in 2 mL of TFA and stirred at room temperature for 3 hours, and a solvent was removed therefrom. The obtained product was purified in accordance with the purification process A to obtain a title compound.

Yield amount: 2 mg
ESI (m/z): 319 [M+H]+

Synthetic Example 12

Synthesis of $N^5$-methyl-$N^5$-(3-sulfophenyl)-L-glutamine (Compound No. 12)

Step 1 Synthesis of 3-[(2-nitrophenyl)sulfonyl]aminobenzenesulfonic acid

3-Aminobenzenesulfonic acid (346.3 mg, 2 mmol) was suspended in 2.5 mL of methylene chloride. After cooling the mixture down to 0° C., 2-nitrophenyl benzensulfonylchloride (443.2 mg, 2 mmol) and N,N-diisopropylethylamine (697 μL, 4 mmol) were added thereto and stirred at room temperature for 1 hour. The solvent was removed therefrom, and purification was conducted in accordance with the purification process A to obtain a title compound.

Yield amount: 460 mg (1.29 mmol) yield: 64%
1H-NMR (DMSO-d6, 300 MHz): δ 7.02-7.83 (m, 8H)
ESI (m/z): 359 [M+H]+

Step 2 Synthesis of $N^5$-methyl-$N^5$-(3-sulfophenyl)-L-glutamine

Potassium carbonate (177 mg, 1.28 mmol), DMF (2 mL) and MeI (60 μL) were added to the compound (230 mg, 0.65 mmol) obtained in step 1, and stirred at 40° C. for 6 hours. Potassium carbonate (44.3 mg) and MeI (40 µL) were further added thereto and stirred overnight. After removing a solvent, purification was conducted in accordance with the purification process A to obtain a crude product (160 mg) of 3-{methyl[(2-nitrophenyl)sulfonyl]amino}benzenesulfonic acid. The crude product (144 mg, 0.39 mmol) was dissolved in DMF (3 mL), and cesium carbonate (126 mg, 0.39 mmol) and thiophenol (40 µL, 0.39 mmol) were added thereto and stirred at 50° C. overnight. After removing a solvent, purification was conducted in accordance with the purification process A to obtain to a crude product (84.1 mg) of 3-(methylamino)benzenesulfonic acid. Then, a title compound was obtained by the same method as that of the synthetic example 1 except that the crude product of 3-(methylamino)benzenesulfonic acid was used instead of 3-sulfoaniline.

Yield amount: 5.14 mg
ESI (m/z): 317 [M+H]+

Synthetic Example 13

Synthesis of O-{[(3-sulfophenyl)amino]carbonyl}-L-serine (Compound No. 13)

Boc-Ser-OtBu (200 mg, 0.77 mmol) was dissolved in 3 mL of methylene chloride and cooled down to 0° C. N,N'-carbonyldiimidazole (124 mg, 0.77 mmol) was added thereto and stirred at room temperature for 2 hours. After removing a solvent, 3-aminobenzenesulfonic acid (132.6 mg, 0.77 mmol), 2 mL of DMF and 0.4 mL of diisopropylethylamine were added thereto and stirred at 70° C. overnight. After removing a solvent, the mixture was purified in accordance with the purification process A to obtain an intermediate. The obtained intermediate was dissolved in 1 mL of TFA and stirred at room temperature for 2 hours. After removing a solvent, purification was conducted in accordance with the purification process A to obtain a title compound.

Yield amount: 1.39 mg yield: 0.6%
ESI (m/z): 304 [M+H]+

Synthetic Example 14

Synthesis of 3-(L-γ-glutamylamino)benzoic acid (Compound No. 14)

Boc-Glu-OtBu (100 mg, 0.33 mmol) and HATU (150.4 mg, 0.40 mmol) were dissolved in 2 mL of DMF. Triethylamine (68.5 µL) was added thereto and stirred for 10 minutes. Ethyl 3-aminobenzoate (49.2 mg, 0.33 mmol) was added thereto and stirred overnight. After liquid separation was conducted with an ethyl acetate and an aqueous solution of 1M sodium hydroxide, the organic layer was washed with an aqueous solution of 1M sodium hydroxide, 1M hydrochloric acid and a saturated saline solution, successively, and dried with sodium sulfate to remove a solvent. The obtained residue was dissolved in 2 mL of THF, 1 mL of ethanol and 1 mL of water, and lithium hydroxide monohydrate (13.5 mg, 0.32 mmol) was added thereto. After stirring the mixture for 5 hours, 4.5 mg of lithium hydroxide was added thereto and stirred overnight. After confirming the completion of the reaction, pH of the reaction solution was adjusted to 2 with 1M hydrochloric acid, and a solvent was removed therefrom. 3 mL of TFA was added to the obtained residue and stirred at room temperature for 5 hours. After removing a solvent, purification was conducted in accordance with the purification process A to obtain a title compound.

Yield amount: 54.17 mg yield: 61%
1H-NMR (D2O, 300 MHz): δ 7.92 (s, 1H), 7.72 (d, 1H, J=7.5 Hz), 7.55 (d, 1H, J=9 Hz), 7.42 (dd, 1H, J=7.5, 9.0 Hz), 4.00-3.80 (m, 1H), 2.58-2.54 (m, 2H), 2.20-2.15 (m, 2H)
ESI (m/z): 267 [M+H]+

Synthetic Example 15

Synthesis of 3-(L-γ-glutamylamino)-2-hydroxybenzoic acid (Compound No. 15)

A title compound was obtained by the same method as that of the synthetic example 14 except that ethyl 3-amino-2-hydroxybenzoate was used instead of ethyl 3-aminobenzoate.

Yield amount: 34.1 mg yield: 37%
1H-NMR (D2O, 300 MHz): δ 7.70-7.60 (m, 2H), 6.87 (t, 1H), 3.91 (t, 1H), 2.63-2.55 (m, 2H), 2.20-2.10 (m, 2H)
ESI (m/z): 283 [M+H]+

Synthetic Example 16

Synthesis of 3-bromo-5-(L-γ-glutamylamino)benzoic acid (Compound No. 16)

A title compound was obtained by the same method as that of the synthetic example 14 except that methyl 3-amino-5-bromobenzoate was used instead of ethyl 3-aminobenzoate.

Yield amount: 16.8 mg
1H-NMR (D2O, 300 MHz): δ 7.80-7.85 (s*2, 2H), 3.75-3.90 (m, 1H), 2.45-2.55 (m, 2H), 2.10-2.20 (m, 2H)
ESI (m/z): 345, 347 [M+H]+

Synthetic Example 17

Synthesis of $N^5$-{3-[hydroxyl(methoxy)phosphoryl]phenyl}-L-glutamine (Compound No. 17)

1-Iodo-3-nitrobenzene (249 mg, 1 mmol) was dissolved in 10 mL of acetonitrile. Tetrakis(triphenylphosphine)palladium (58 mg, 3 mol %), dimethyl phosphite (0.138 ml, 1.5 mmol) and triethylamine (0.28 ml, 2 mmol) were added thereto and stirred at 70° C. overnight. After removing a solvent, the mixture was purified in accordance with the purification process A to obtain a mixture (0.222 g) of monomethyl (3-nitrophenyl) phosphonate and dimethyl ester. The obtained monomethyl phosphonate was dissolved in 10 mL of methanol. Pd/C in catalyst quantity was added thereto and stirred under hydrogen atmosphere overnight. After filtering out the catalyst, a solvent was removed to obtain a mixture of monomethyl (3-aminophenyl) phosphonate and dimethyl ester.

Boc-Glu-OtBu (303 mg, 1 mmol), HOAt (136 mg, 1 mmol) and HATU (380 mg, 1 mmol) were dissolved in 1 mL of DMF, and triethylamine (0.278 ml) was added thereto. 10 minutes later, the mixture of monomethyl (3-aminophenyl) phosphonate and dimethyl ester was added thereto and stirred at room temperature overnight. After removing a solvent, purification was conducted in accordance with the purification process A to obtain a title compound.

Yield amount: 11.5 mg
1H-NMR (D2O, 300 MHz): δ 7.50-7.90 (m, 4H), 4.14-4.18 (m, 1H), 3.56 (s, 1.5H), 3.52 (s, 1.5H), 2.68-2.74 (m, 2H), 2.280-2.37 (m, 2H)
ESI (m/z): 317 [M+H]+

Synthetic Example 18

Synthesis of $N^5$-(3-phosphonophenyl)-L-glutamine (Compound No. 18)

4 mL of DMF and trimethylsilyl bromide (1 mL) were added to the mixture (170 mg) of monomethyl (3-nitrophenyl) phosphonate and dimethyl ester, and stirred at 60° C. for 2 hours. After removing a solvent, the mixture was dissolved in a mixed solvent of water and methanol. Pd/C in catalyst quantity was added thereto and stirred under hydrogen atmosphere overnight. After filtering out the catalyst, a solvent was removed to obtain a crude product of (3-aminophenyl)phosphonic acid.

Boc-Glu-OtBu (236 mg, 0.78 mmol), HOAt (127 mg, 0.936 mmol) and HATU (356 mg, 0.936 mmol) were dissolved in 1 mL of DMF, and triethylamine (0.21 ml) was added thereto. 10 minutes later, the crude product of (3-aminophenyl)phosphonic acid was added thereto and stirred at room temperature overnight. After removing a solvent, purification was conducted in accordance with the purification process A to obtain a title compound.

Yield amount: 2.5 mg
ESI (m/z): 303 [M+H]+

Synthetic Example 19

Synthesis of $N^5$-(3-nitrophenyl)-L-glutamine (Compound No. 19)

A title compound was obtained by the same method as that of the synthetic example 1 except that 3-nitroaniline was used instead of 3-sulfoaniline.

Yield amount: 61.6 mg yield: 93%
1H-NMR (DMSO-d6, 300 MHz): δ 10.5 (s, 1H), 8.66 (s, 1H), 7.86-7.93 (m, 2H), 7.61 (t, 1H, J=8.2 Hz), 3.99 (t, 1H, J=6.2 Hz), 2.50-2.70 (m, 2H), 2.06-2.16 (m, 2H) ESI (m/z): 268 [M+H]+

Synthetic Example 20

N-γ-glutamyl-aniline (Compound No. 20)

The product purchased from Bachem was used as the compound No. 20.

The following examples will further illustrate synthesis of the other representative compounds of the present invention shown in Table 2. They only explain the compounds of the present invention and do not particularly limit them.

TABLE 2 (I)

| Comp. No. | $R_1$ | $R_2$ | $R_3$ | $R_4$ | $R_5$ | $R_6$ | X |
|---|---|---|---|---|---|---|---|
| 21 | H | $SO_3H$ | Me | Cl | H | H | $CH_2$ |
| 22 | H | $SO_3H$ | H | Cl | Me | H | $CH_2$ |
| 23 | OH | $SO_3H$ | H | $NO_2$ | H | H | $CH_2$ |
| 24 | Cl | $CO_2H$ | H | Cl | H | H | $CH_2$ |
| 25 | Cl | $CO_2H$ | H | H | H | H | $CH_2$ |
| 26 | H | $CO_2H$ | H | H | Cl | H | $CH_2$ |
| 27 | OMe | $CO_2H$ | H | H | H | H | $CH_2$ |
| 28 | H | $CO_2H$ | OH | H | H | H | $CH_2$ |
| 29 | H | $CO_2H$ | H | H | Me | H | $CH_2$ |
| 30 | H | $CO_2H$ | H | OH | H | H | $CH_2$ |
| 31 | Me | $CO_2H$ | H | H | H | H | $CH_2$ |
| 32 | H | $CO_2H$ | H | Cl | H | H | $CH_2$ |
| 33 | H | $SO_3H$ | Me | Cl | H | H | O |
| 34 | OH | $SO_3H$ | H | Cl | H | H | O |
| 35 | H | $SO_3H$ | H | Cl | Me | H | O |
| 36 | OMe | $SO_3H$ | H | Cl | H | H | O |
| 37 | H | $SO_3H$ | H | H | Cl | H | $CH_2$ |
| 38 | H | H | $SO_3H$ | Cl | H | H | $CH_2$ |
| 39 | $SO_3H$ | H | H | Br | H | H | $CH_2$ |
| 40 | H | H | $SO_3H$ | I | H | H | $CH_2$ |
| 41 | $SO_3H$ | H | H | I | H | H | $CH_2$ |
| 42 | H | $SO_3H$ | H | H | H | OH | $CH_2$ |
| 43 | H | $SO_3H$ | H | H | H | OH | O |

Synthetic Example 21

Synthesis of $N^5$-(3-chloro-4-methyl-5-sulfophenyl)-L-glutamine (Compound No. 21)

1 mL of Methylene chloride and 1 mL of THF were added to 303 mg (1 mmol) of Boc-Glu-OtBu hydrochloride and 180 mg (1.1 mmol) of CDI. 221 mg of 5-Amino-3-chloro-2-methylbenzenesulfonic acid was added thereof and stirred at room temperature overnight. Purification was conducted in accordance with the purification process A to obtain a protected form of the intended compound. The obtained protected form was dissolved in 5 mL of a trifluoroacetic acid and stirred for 2 hours. After removing a solvent, purification was conducted in accordance with the purification process A to obtain a title compound.

1H-NMR (D2O) δ: 7.71 (d, 1H), 7.60 (d, 1H), 3.93 (t, 1H), 2.50-2.57 (m, 2H), 2.47 (s, 3H), 2.10-2.20 (m, 2H)
ESI-MS: 349 [M−H]−, 351 [M+H]+

Synthetic Example 22

Synthesis of $N^5$-(3-chloro-2-methyl-5-sulfophenyl)-L-glutamine (Compound No. 22)

2 mL of DMF and 0.52 mL (3 mmol) of DIEA were added to 303 mg (1 mmol) of Boc-Glu-OtBu hydrochloride, 221 mg (1 mmol) of 3-amino-5-chloro-4-methylbenzenesolfonic acid, 160 mg (1.3 mmol) of HOAt and 410 mg (1.3 mmol) of HATU, and stirred at room temperature overnight. The reaction solution was diluted with water-acetonitrile and purified in accordance with the purification process A to obtain a protected form of the intended compound. The obtained protected form was dissolved in 5 mL of a trifluoroacetic acid and stirred for 2 hours. After removing a solvent, purification was conducted in accordance with the purification process A to obtain a title compound.

Yield amount: 150 mg

1H-NMR (D2O) δ: 7.81 (d, 1H), 7.61 (d, 1H), 4.10 (t, 1H), 2.74-2.81 (m, 2H), 2.24-2.37 (m, 5H)

ESI-MS: 349 [M−H]−, 351 [M+H]+

Synthetic Example 23

Synthesis of $N^5$-(2-hydroxy-5-nitro-3-sulfophenyl)-L-glutamine (Compound No. 23)

A title compound was obtained by the same method as that of the synthetic example 22 except that 3-amino-2-hydroxy-5-nitrobenzenesolfonic acid was used instead of 3-amino-5-chloro-4-methylbenzenesolfonic acid.

Yield amount: 185 mg

1H-NMR (D2O) δ: 8.55 (d, 1H, J=2.4 Hz), 8.29 (d, 1H, J=2.7 Hz), 3.95 (t, 1H, J=6.3 Hz), 2.66 (t, 2H, J=7.2 Hz), 2.10-2.30 (m, 2H)

ESI-MS: 362 [M−H]−, 364 [M+H]+

Synthetic Example 24

Synthesis of 2,5-dichloro-3-(L-γ-glutamylamino)benzoic acid (Compound No. 24)

(Step 1)

206 mg (1.0 mmol) of 2,5-Dichloro-3-aminobenzoic acid was dissolved in 4 mL of acetone. 0.7 mL (1.4 mmol) of A hexane solution of 2.0M trimethylsilyldiazomethane was added thereto and stirred at room temperature for 1.5 hours. A solvent was removed to obtain methyl 2,5-dichloro-3-aminobenzoate.

Yield amount: 220 mg (Step 2)

190 mg (0.5 mmol) of HATU, 70 mg (0.5 mmol) of HOAt, 152 mg (0.5 mmol) of Boc-Glu-OtBu hydrochloride, 0.21 mL (1.5 mmol) of triethylamine and 2 mL of dichloromethane were added to 110 mg (0.5 mmol) of methyl 2,5-dichloro-3-aminobenzoate, and stirred at room temperature overnight.

After removing a solvent, the mixture was extracted with ethyl acetate-water. The organic layer thereof was treated with a saturated saline solution and dried with sodium sulfate. After filtering out sodium sulfate and removing a solvent, 5 mL of 1N sodium hydroxide solution was added thereto and stirred at room temperature for 2 hours. Then, 5 mL of a trifluoroacetic acid was added thereto and stirred at room temperature for 2 hours. After removing a solvent, purification was conducted in accordance with the purification process A to obtain a title compound.

Yield amount: 6.6 mg

1H-NMR (CD3OD) δ: 8.08 (s, 1H), 7.56 (s, 1H), 3.95-4.01 (m, 1H), 2.76-2.82 (m, 2H), 2.20-2.30 (m, 2H)

ESI-MS: 333 [M−H]−, 335 [M+H]+

Synthetic Example 25

Synthesis of 2-chloro-3-(L-γ-glutamylamino)benzoic acid (Compound No. 25)

A title compound was obtained by the same method as that of the synthetic example 24 (synthesis of Compound No. 24) except that 2-chloro-3-aminobenzoic acid was used instead of the benzoic acid derivative.

Yield amount: 4.0 mg

1H-NMR (D2O) δ: 7.47-7.56 (m, 1H), 7.39-7.46 (m, 1H), 7.27-7.32 (s, 1H), 3.81-387 (m, 1H), 2.59-2.65 (m, 2H), 2.12-2.21 (m, 2H)

ESI-MS: 299 [M−H]−, 301 [M+H]+

Synthetic Example 26

Synthesis of 4-chloro-3-(L-γ-glutamylamino)benzoic acid (Compound No. 26)

A title compound was obtained by the same method as that of the synthetic example 24 (synthesis of Compound No. 24) except that 4-chloro-3-aminobenzoic acid was used instead of the benzoic acid derivative.

Yield amount: 5.3 mg

1H-NMR (D2O) δ: 8.03 (s, 1H), 7.76-7.79 (m, 1H), 7.52-7.55 (m, 1H), 3.78-3.84 (m, 1H), 2.59-2.65 (m, 2H), 2.12-2.22 (m, 2H)

ESI-MS: 299 [M−H]−, 301 [M+H]+

Synthetic Example 27

Synthesis of 2-methoxy-3-(L-γ-glutamylamino)benzoic acid (Compound No. 27)

84 mg (0.2 mmol) of HATU, 30 mg (0.2 mmol) of HOAt, 61 mg (0.2 mmol) of Boc-Glu-OtBu hydrochloride, 0.084 mL (0.6 mmol) of triethylamine and 1 mL of dichloromethane were added to 36 mg (0.2 mmol) of methyl 2-methoxy-3-aminobenzoate, and stirred at room temperature overnight.

After removing a solvent, the mixture was extracted with ethyl acetate-water. The organic layer thereof was treated with a saturated saline solution and dried with sodium sulfate. After filtering out sodium sulfate and removing a solvent, 5 mL of 1N sodium hydroxide solution was added thereto and stirred at room temperature for 2 hours. Then, 5 mL of a trifluoroacetic acid was added thereto and stirred at room temperature for 2 hours. After removing a solvent, purification was conducted in accordance with the purification process A to obtain a title compound.

Yield amount: 6.5 mg

1H-NMR (D2O) δ: 7.69-7.71 (m, 1H), 7.56-7.59 (m, 1H), 7.13-7.18 (m, 1H), 3.87-3.93 (m, 1H), 3.68 (s, 3H), 2.60-2.66 (m, 2H), 2.12-2.22 (m, 2H)

ESI-MS: 295 [M−H]−, 297 [M+H]+

Synthetic Example 28

Synthesis of 6-hydroxy-3-(L-γ-glutamylamino)benzoic acid (Compound No. 28)

6-methoxy-3-(L-γ-glutamylamino)benzoic acid was synthesized by the same method as that of the synthetic example 27 (synthesis of Compound No. 27) except that 6-methoxy-3-aminobenzoic acid was used instead of the benzoic acid derivative. Then, purification was conducted in accordance with the purification process A to obtain a title compound that is obtained as a by-product in the synthetic process.

Yield amount: 2.1 mg
ESI-MS: 280 [M−H]−, 282 [M+H]+

Synthetic Example 29

Synthesis of 4-methyl-3-(L-γ-glutamylamino)benzoic acid (Compound No. 29)

500 mg of 4-Methyl-3-nitrobenzoic acid was dissolved in 5 mL of methanol and 10 mL of a dioxane solution containing 4N hydrogen chloride. After stirring the mixture at room temperature for 2 days, a solvent was removed to obtain a crude product. The obtained crude product was dissolved in 10 mL of methanol, and Pd/C in catalyst quantity was acted thereon under hydrogen atmosphere at room temperature overnight. After filtering out the catalyst, a solvent was removed to obtain a crude product. 165 mg of the obtained crude product, 303 mg (1 mmol) of Boc-Glu-OtBu hydrochloride and 400 mg (about 1.3 mmol) of HATU were dissolved in 1 mL of DMF. 0.26 mL of DIEA was added thereto and stirred overnight. The reaction solution was diluted with water-acetonitrile and purified in accordance with the purification process A to obtain 0.31 g of a protected form of the intended compound. 3 mL of THF, 1.5 mL of methanol and 1.5 mL of water were added to the obtained protected form, and then 26 mg (0.82 mmol) of lithium hydroxide monohydrate was further added thereto. After stirring the mixture for 2 hours, a solvent was removed. 3 mL of THF, 1.5 mL of methanol and 1.5 mL of water were again added thereto, then 26 mg (0.82 mmol) of lithium hydroxide monohydrate was further added thereto and stirred for 2 hours. After adding 2 mL of ethyl acetate thereto, a solvent was removed. Then, 3 mL of a trifluoroacetic acid was added thereto and stirred at room temperature for 2 hours. After removing a solvent, purification was conducted in accordance with the purification process A to obtain a title compound.

1H-NMR (D2O) δ: 7.74-7.77 (m, 1H), 7.30-7.36 (m, 1H), 3.75-3.81 (m, 1H), 2.55-2.62 (m, 2H), 2.10-2.20 (m, 5H)
ESI-MS: 279 [M−H]−, 281 [M+H]+

Synthetic Example 30

Synthesis of 5-hydroxy-3-(L-γ-glutamylamino)benzoic acid (Compound No. 30)

5-methoxy-3-(L-γ-glutamylamino)benzoic acid was synthesized by the same method as that of the synthetic example 27 (synthesis of Compound No. 27) except that 5-methoxy-3-aminobenzoic acid was used instead of the benzoic acid derivative. Then, purification was conducted in accordance with the purification process A to obtain a title compound that is obtained as a by-product in the synthetic process.

Yield amount: 7.5 mg
ESI-MS: 280 [M−H]−, 282 [M+H]+

Synthetic Example 31

Synthesis of 3-(L-γ-glutamylamino)-2-methyl-benzoic acid (Compound No. 31)

A title compound was obtained by the same method as that of the synthetic example 29 (synthesis of Compound No. 29) except that 2-methyl-3-nitrobenzoic acid was used instead of the benzoic acid derivative.

Yield amount: 37 mg
1H-NMR (D2O) δ: 7.56 (dd, 1H), 7.30 (dd, 1H), 7.23 (t, 1H), 3.82 (t, 1H), 2.5-2.62 (m, 2H), 2.21 (s, 3H), 2.10-2.29 (m, 2H)
ESI-MS: 279 [M−H]−, 281 [M+H]+

Synthetic Example 32

Synthesis of 5-chloro-3-(L-γ-glutamylamino)benzoic acid (Compound No. 32)

(Step 1)
8 mL of methanol and 2 mL of THF were added to 228 mg (1 mmol) of methyl 5-chloro-1,3-dibenzoate and 56 mg (1 mmol) of potassium hydroxide, and stirred at room temperature overnight. The reaction solution was concentrated under reduced pressure. 4 mL of Toluene, 0.12 mL (0.85 mmol) of triethylamine and 0.19 mL (0.88 mmol) of diphenylphosphoryl azide were added thereto and stirred at 50° C. for 1 hour. Then, 0.19 mL (2 mmol) of t-butyl alcohol and 2 mL of toluene were added thereto and stirred at 80° C. overnight. After cooling the mixture down to room temperature, it was extracted with ethyl acetate-water. The organic layer thereof was treated with a saturated saline solution and dried with sodium sulfate. After filtering out sodium sulfate and removing a solvent, purification was conducted in accordance with the purification process A to obtain methyl 5-chloro-3-aminobenzoate-trifluoroacetate.

Yield amount: 30 mg
(Step 2)
38 mg (0.1 mmol) of HATU, 14 mg (0.1 mmol) of HOAt, 30 mg (0.1 mmol) of Boc-Glu-OtBu hydrochloride, 0.014 mL (0.1 mmol) of triethylamine and 1 mL of dichloromethane were added to 30 mg (0.1 mmol) of methyl 5-chloro-3-aminobenzoate, and stirred at room temperature overnight.

After removing a solvent, the mixture was extracted with ethyl acetate-water. The organic layer thereof was treated with a saturated saline solution and dried with sodium sulfate. After filtering out sodium sulfate and removing a solvent, 5 mL of 1N sodium hydroxide solution was added thereto and stirred at room temperature for 2 hours. Then, 5 mL of a trifluoroacetic acid was added thereto and stirred at room temperature for 2 hours. After removing a solvent, purification was conducted in accordance with the purification process A to obtain a title compound.

Yield amount: 1.0 mg
1H-NMR (D2O) δ: 7.54 (s, 1H), 7.48 (s, 1H), 7.45 (s, 1H), 3.96-4.00 (m, 1H), 2.50-2.56 (m, 2H), 2.12-2.20 (m, 2H)
ESI-MS: 299 [M−H]−, 301 [M+H]+

Synthetic Example 33

Synthesis of O-{[(3-chloro-4-methyl-5-sulfophenyl)amino]carbonyl}-L-serine (Compound No. 33)

100 mg (0.38 mmol) of Boc-Ser-OtBu, 86 mg (0.38 mmol) of 5-amino-3-chloro-2-methylbenzenesulfonic acid and 37 mg (0.0127 mmol) of triphosgene were suspended in 1 mL of methylene chloride, and 66 μL (0.76 mmol) of DIEA was added thereto. After stirring the mixture at room temperature overnight, a solvent was removed. Purification was conducted in accordance with the purification process A to obtain a protected form of a title compound. The obtained protected form was dissolved in 2 mL of a trifluoroacetic acid and stirred for 2 hours. After removing a solvent, purification was conducted in accordance with the purification process A to obtain a title compound.

Yield amount: 15.5 mg
1H-NMR (D2O) δ: 7.67 (d, 1H), 7.57 (d, 1H), 4.51 (t, 2H), 4.15 (dd, 1H), 2.47 (s, 3H)
ESI-MS: 351 [M−H]−, 353 [M+H]+

Synthetic Example 34

Synthesis of sodium 3-{[(2S)-2-amino-2-carboxyethoxycarbonyl]amino}-5-chloro-2-hydroxybenzenesulfonate (Compound No. 34)

The same method was used as that of the synthetic example 33 (synthesis of Compound No. 33) except that 3-amino-5-chloro-2-hydroxybenzenesulfonic acid was used instead of the benzenesulfonic acid derivative. Then, 1 equivalent of an aqueous solution of 0.1N sodium hydroxide was added thereto and freeze-dried to obtain a title compound.
Yield amount: 15.1 mg
1H-NMR (D2O) δ: 7.70 (s, 1H), 7.37 (d, 1H, J=2.6 Hz), 4.37-4.55 (m, 2H), 3.98 (dd, 1H, J=3.0, 5.3 Hz),
ESI-MS: 353 [M−H]−, 355 [M+H]+

Synthetic Example 35

Synthesis of O-{[(3-chloro-2-methyl-5-sulfophenyl)amino]carbonyl}-L-serine (Compound No. 35)

A title compound was obtained by the same method as that of the synthetic example 33 (synthesis of Compound No. 33) except that 3-amino-5-chloro-4-methylbenzenesulfonic acid was used instead of the benzenesulfonic acid derivative.
Yield amount: 3.9 mg
1H-NMR (D2O) δ: 7.60-7.64 (m, 2H), 4.42-4.54 (m, 2H), 4.03 (dd, 1H, J=3.2, 4.8 Hz)
ESI-MS: 351 [M−H]−, 353 [M+H]+

Synthetic Example 36

Synthesis of O-{[(5-chloro-2-methoxy-3-sulfophenyl)amino]carbonyl}-L-serine (Compound No. 36)

2 mL of acetone was added to 30 mg of a protected form obtained in the synthetic example 34 (synthesis of Compound No. 34). 1 mL of A hexane solution containing 2M trimethylsilyldiazomethane and 100 μL of triethylamine were further added thereto. After stirring the mixture for 20 minutes, a solvent was removed. Then, the mixture was purified in accordance with the purification process A to obtain a methylated form. The obtained methylated form was dissolved in 2 mL of a trifluoroacetic acid and stirred at room temperature for 3 hours. After removing a solvent, water was added thereto and freeze-dried to obtain a title compound.
Yield amount: 1.48 mg
1H-NMR (D2O) δ: 7.64 (brs, 1H), 7.27 (d, 1H, J=2.6 Hz), 4.25-4.22 (m, 2H), 3.80 (dd, 1H, J=3.1, 5.0 Hz), 3.52 (s, 3H)

Synthetic Example 37

Synthesis of $N^5$-(2-chloro-5-sulfophenyl)-L-glutamine (Compound No. 37)

2 mL of methanol and 3 mL of water were added to sodium 4-chloro-3-nitrobenzensulfonate (1 mmol). 2% Pt—S/C in catalyst quantity was added thereto and stirred under hydrogen atmosphere overnight at room temperature. After filtering out the catalyst, the mixture was sufficiently dried. Then, 303 mg (1 mmol) of Boc-Glu-OtBu hydrochloride, 163 mg (1.2 mmol) of HOAt, 456 mg (1.2 mmol) of HATU, 2 mL of DMF and 0.35 mL of DIEA were added thereto and stirred at room temperature overnight. The reaction solution was diluted with water-acetonitrile and purified in accordance with the purification process A to obtain a protected form of a title compound. The obtained protected form was dissolved in 3 mL of a trifluoroacetic acid and stirred at room temperature for 2 hours. After removing a solvent, purification was conducted in accordance with the purification process A to obtain a title compound.
Yield amount: 69.9 mg
1H-NMR (D2O) δ: 7.85 (brs, 1H), 7.50-7.55 (m, 2H), 4.03 (t, 1H), 2.66 (t, 2H, J=7.1 Hz), 2.10-2.30 (m, 2H)
ESI-MS: 335 [M−H]−, 337 [M+H]+

Synthetic Example 38

Synthesis of $N^5$-(3-chloro-4-sulfophenyl)-L-glutamine (Compound No. 38)

Step 1

0.4 mL of 3-chloroaniline was slowly added to 4 mL of a fuming sulfuric acid and stirred at room temperature overnight. Cooling it down to 0° C., the reaction solution was poured in water, and a precipitated solid substance was taken by filtration. The solid substance was dissolved in an aqueous solution of 2N sodium hydroxide. Then, a concentrated hydrochloric acid wad added thereto to make the liquid acidic. The precipitated solid substance was filtered out to obtain a crude product of 4-amino-2-chlorobenzenesulfonic acid.
Yield amount: 80 mg Step 2

A title compound was obtained by the same method as that of the synthetic example 21 (synthesis of Compound No. 21) except that the crude product of 4-amino-2-chlorobenzenesulfonic acid obtained in the step 1 was used instead of the benzenesulfonic acid derivative.
Yield amount: 40 mg
1H-NMR (D2O) δ: 7.80 (d, 1H), 7.63 (d, 1H), 7.33 (dd, 1H), 3.94 (t, 1H), 2.50-2.60 (m, 2H), 2.10-2.22 (m, 2H)
ESI-MS: 337 [M+H]+, 335 [M−H]−

Synthetic Example 39

Synthesis of $N^5$-(5-bromo-2-sulfophenyl)-L-glutamine (Compound No. 39)

A title compound was obtained by the same steps as those of the synthetic example 38 (synthesis of Compound No. 38) except that 3-bromoaniline was used instead of the aniline derivative used in the step 1 of the example 38.
Yield amount: 9.9 mg
ESI-MS: 429 [M+H]+, 427 [M−H]−

Synthetic Example 40

Synthesis of $N^5$-(3-iodo-4-sulfophenyl)-L-glutamine (Compound No. 40)

A title compound was obtained by the same steps as those of the synthetic example 38 (synthesis of Compound No. 38) except that 3-iodoaniline was used instead of the aniline derivative used in the step 1 of the example 18.

Yield amount:

1H-NMR (D2O) δ: 8.12 (s, 1H), 7.84 (d, 1H), 7.44 (dd, 1H), 3.75-3.90 (m, 1H), 2.50-2.60 (m, 2H), 2.00-2.20 (m, 2H)

ESI-MS: 429 [M+H]+, 427 [M−H]−

Synthetic Example 41

Synthesis of $N^5$-(5-iodo-2-sulfophenyl)-L-glutamine (Compound No. 41)

This compound was obtained as a regioisomer in the synthetic example 40.

Yield amount:

1H-NMR (D2O) δ: 8.11 (d, 1H), 7.63-7.66 (m, 1H), 7.48 (d, 1H), 3.80-3.90 (m, 1H), 2.58-2.66 (m, 2H), 2.10-2.24 (m, 2H)

ESI-MS: 429 [M+H]+, 427 [M−H]−

Synthetic Example 42

Synthesis of $N^5$-hydroxy-$N^5$-(3-sulfophenyl)-L-glutamine (Compound No. 42)

270 mg (4.3 mmol) of zinc powder and 106 mg (2 mmol) of ammonium chloride were suspended in 2 mL of a mixed solvent of methanol:water=1:1. 450 mg (2 mmol) of sodium 2-nitrobenzenesulfonate was slowly added thereto. After heating the mixture up to 65° C. and stirring it for 1 hour, an insoluble substance was filtered, and the obtained filtrate was removed to obtain a crude product of a hydroxylamine derivative. 5 mL of DMF and 0.35 mL of DIEA were added to 450 mg (1.5 mmol) of Boc-Glu-OtBu hydrochloride, 230 mg (1.7 mmol) of HOAt and 646 mg (1.7 mmol) of HATU, and stirred for 10 minutes. Then, the solution was added to the obtained crude product and stirred overnight. Purification was conducted in accordance with the purification process A to obtain a protected form of a title compound. 4 mL of TFA was added to the obtained protected form and stirred for 2 hours. After removing TFA, purification was conducted in accordance with the purification process A to obtain a title compound.

Yield amount: 135 mg

1H-NMR (DMSO) δ: 10.65 (s, 1H), 10.04 (s, 1H), 7.20-8.40 (m, 7H), 3.90-4.10 (m, 1H), 2.60-3.00 (m, 2H), 1.90-2.20 (m, 2H)

ESI-MS: 317 [M−H]−, 319 [M+H]+

Synthetic Example 43

Synthesis of O-{[hydroxy(3-sulfophenyl)amino]carbonyl}-L-serine (Compound No. 43)

2 mL of Methylene chloride and 0.35 mL of DIEA were added to Boc-Ser-OtBu (1 mmol), the crude product of hydroxylamine obtained in synthetic example 42 and 100 mg (0.33 mmol) of triphosgene, and stirred at room temperature overnight. After removing a solvent, the obtained residue was purified in accordance with the purification process A to obtain a protected form of a title compound. The obtained protected form was dissolved in 4 mL of TFA and stirred at room temperature for 3 hours. After removing TFA, purification was conducted in accordance with the purification process A to obtain a title compound.

Yield amount: 6.6 mg

1H-NMR (D2O) δ: 7.78-7.80 (m, 1H), 7.43-7.60 (m, 4H), 4.56-4.58 (m, 2H), 4.10-4.15 (m, 1H)

ESI-MS: 319 [M−H]−, 321 [M+H]+

Example II

Preparation of a CaSR Gene

A CaSR gene was prepared as follows. Based on the DNA sequence registered in NCBI (CaSR (calcium receptor): NM_000388, Seq. Nos. 1-2), synthetic oligo DNA used in PCR was synthesized (forward primer (Seq. No. 3: ACT-AATACGACTCACTATAGGGACCATG-GCATTTTATAGCTGCTGCTGG) and reverse primer (Seq. No. 4: TTATGAATTCACTACGTTTTCTGTAACAG).

PCR was conducted under following conditions by using as a material cDNA derived from human kidney (by Clontech) and also using the above primers and Pfu Ultra DNA Polymerase (by Stratagene). The reactions at 94° C. for 3 minutes, at 94° C. for 30 seconds, at 55° C. for 30 seconds and at 72° C. for 2 minutes were repeated 35 times, and the reaction at 72° C. for 7 minutes was conducted. Agarose electrophoresis was conducted to confirm whether the intended product was amplified by PCR, and the product was dyed in DNA dyeing test and then detected with ultraviolet irradiation. At the same time, a chain length of the PCR product was confirmed by comparing it with a DNA marker to which electrophoresis was conducted and of which size is known. Plasmid vector pBr322 was cut by restriction enzyme EcoRV (by Takara). The gene fragment amplified by PCR was connected with Ligation kit (by Promega) to the cut part. E. coli DH5α was transformed in the reaction solution, and the transformant holding a plasmid cloning the product amplified by PCR was selected. It was confirmed by DNA sequence analysis that the product amplified by PCR comprises a CaSR gene. Plasmid expressing human CaSR: hCaSR/pcDNA3.1 was prepared by using this recombinant plasmid.

Example III

Evaluation of CaSR Agonistic Activity (Method of Evaluating a CaSR Agonist)

293E cells (HEK293 cell expressing EBNA1, ATCC No. CRL-10852) were cultured in DMEM containing 10% fetal bovine serum (Dulbecco's modified Eagle medium containing 1.0 g/mL Glucose, by NACALAI TESQUE, INC.), in the presence of 250 μg/mL of G418. The cells were spread on a petri dish of 10 cm diameter in $1.8 \times 10^6$ cells/15 mL. After leaving them in the $CO_2$ incubator (5% $CO_2$, 37° C.) for 24 hours, plasmid expressing human CaSR: hCaSR/pcDNA3.1 was transfected with a transfection reagent: Mirus TransIT 293 (by Takara Bio Inc.). After leaving it in the $CO_2$ incubator for 24 hours, the cells were collected by DMEM containing 10% fetal bovine serum and seeded on poly-D-lysine coat 384 well plate (by Falcon) in 15,000 cells/well. After leaving them in the $CO_2$ incubator for 24 hours, the medium was removed. Then, 50 μL/well of $Ca^{2+}$ fluorescent indicator: Calcium 4 Assay Kit (by Molecular Devices) that was dissolved in an assay buffer (146 mM NaCl, 5 mM KCl, 1 mM $MgSO_4$, 1 mg/mL Glucose, 20 mM HEPES (pH 7.2), 1.5 mM $CaCl_2$) was added thereto, and left at 37° C. for 1 hour and at room temperature for 30 minutes to absorb the fluorescent indicator. The 384 well plate was transferred to FLIPR (by Molecular Devices). Then, 12.5 μL/well of a compound that was dissolved in a 0.1% BSA containing assay buffer was added thereto, and change in fluorescence intensity was measured for 3 minutes. Meanwhile, Compound No. 20 was purchased from Bachem.

(Method of Calculating $EC_{50}$)

The difference between the maximum value and the minimum value (RFU(Max−Min)) of the fluorescence intensity before and after adding a compound was automatically calculated by FLIPR. RFU(Max−Min) when adding a compound in maximum concentration was defined as 100%; and RFU(Max−Min) when adding DMSO instead of the compound in the same concentration as that of the compound was defined as 0%. Based on them, activation rate was calculated, and curve-fitting was conducted by spreadsheet Xfit to calculate $EC_{50}$ that is a concentration of the compound having activation rate 50%. Tables 3 and 4 show the results of the compounds shown in Tables 1 and 2.

TABLE 3

| Comp. No. | $EC_{50}[\mu M]$ |
|---|---|
| 1 | 0.012 |
| 2 | 2.3 |
| 3 | 0.56 |
| 4 | 0.059 |
| 5 | 0.13 |
| 6 | 2.7 |
| 7 | 0.0019 |
| 8 | 0.10 |
| 9 | 0.27 |
| 10 | 0.017 |
| 11 | 0.086 |
| 12 | 0.20 |
| 13 | 0.072 |
| 14 | 2.0 |
| 15 | 0.034 |
| 16 | 0.048 |
| 17 | 2.0 |
| 18 | 0.53 |
| 19 | 0.40 |
| 20 | 0.94 |

TABLE 4

| Comp. No. | $EC_{50}[\mu M]$ |
|---|---|
| 21 | 0.0057 |
| 22 | 0.0014 |
| 23 | 0.89 |
| 24 | 0.022 |
| 25 | 0.97 |
| 26 | 0.16 |
| 27 | 0.15 |
| 28 | 0.33 |
| 29 | 0.53 |
| 30 | 2.9 |
| 31 | 3.7 |
| 32 | 0.0088 |
| 33 | 0.0021 |
| 34 | 0.0019 |
| 35 | 0.0037 |
| 36 | 3.5 |
| 37 | 0.0029 |
| 38 | 6.7 |
| 39 | 5.0 |
| 40 | 7.9 |
| 41 | 2.3 |
| 42 | 0.031 |
| 43 | 0.043 |

Example IV

Effect of a CaSR Agonist on Water Absorption in Rat Large Intestine Loop Method (1)

(Method)

The cecum and large intestine were taken out from the abdomen of a male SD (IGS) rat under pentobarbital anesthesia, and a large intestine loop was prepared by ligating a part 5 cm just below the cecum. Immediately after preparing the loop, PGE2 (4 μg/mL/kg, SIGMA) was intraperitoneally administered. 30 minutes later, 2 mL of Tyrode solution (NaCl 136.9 mM, KCl 2.7 mM, $CaCl_2.2H_2O$ 1.8 mM, $MgCl_2.6H_2O$ 1.04 mM, $NaH_2PO_4.2H_2O$ 0.04 mM, glucose 5.55 mM, $NaHCO_3$ 11.9 mM) was poured in the prepared loop. 1 hour later, the weight of the loop, the weight thereof when the liquid was removed from the loop, and the loop area were measured to calculate the weight per unit area of the liquid that remains in the loop.

A test compound was tested by dissolving it in Tyrode solution that was adjusted to pH 6.5 to 7.5.

The remaining liquid weight per unit area ($g/cm^2$) was calculated by the following formula.

Remaining liquid weight per unit area ($g/cm^2$)=(loop weight−loop weight when the liquid was removed from the loop)/loop area Water absorption was evaluated by calculating the inhibition ratio by the following formula.

Inhibition ration (%)=100−(remaining liquid weight per unit area with a drug−basic average remaining liquid weight per unit area)/(average remaining liquid weight per unit area of vehicle−basic average remaining liquid weight per unit area)× 100

The results are shown in FIG. 1. The water absorption of the compound No. 1 in Table 1 was promoted in a dose-dependent manner, and thus, it was indicated that the compound is useful as a therapeutic or preventive agent for diarrhea.

Example V

Effect of a CaSR Agonist on Water Absorption in Rat Large Intestine Loop Method (2)

Figure 2:
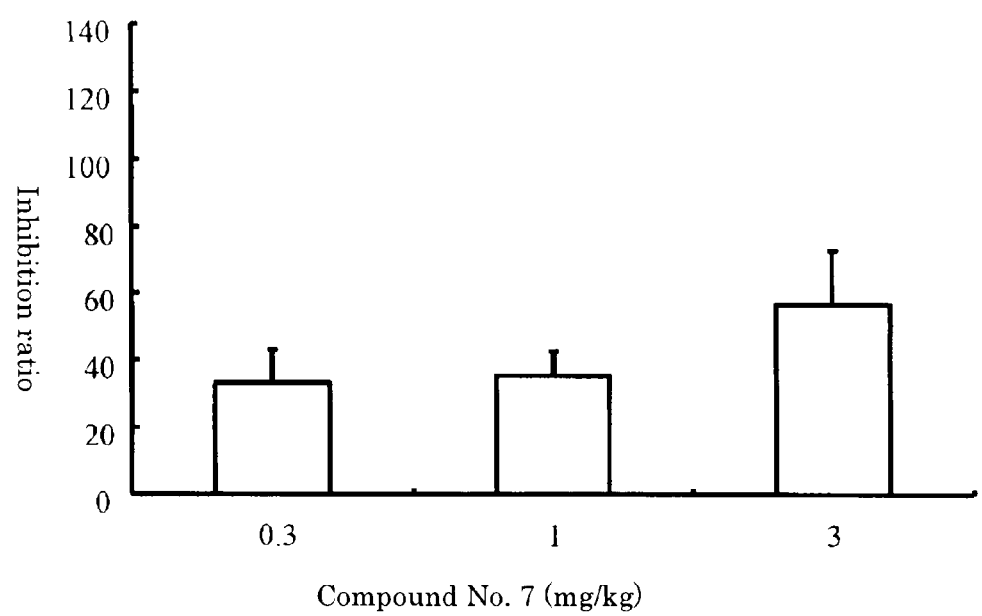
FIG. 2 shows a diagram of the prophylactic activity of Compound No. 7 on diarrhea.

The same test was conducted on a compound No. 7 as the method of Example IV. The results are shown in FIG. 2. The water absorption of the compound No. 7 in Table 1 was promoted in a dose-dependent manner, and thus, it was indicated that the compound is useful as a therapeutic or preventive agent for diarrhea.

Example VI

Test Example 1

Evaluation of "Kokumi" Taste

<Kokumi-Imparting Activities of Compounds (Sodium Salts of Compound Nos. 1 and 7) Used in the Present Invention>

On compounds wherein a calcium receptor activating action was found (sodium salts of Compound Nos. 1, 7 and 21), the intensity of kokumi-imparting activity was examined by a quantitative sensory evaluation test. The used compound was prepared by dissolving 525 mg of the compound No. 1 described in Synthetic Example 1 of Example I in 5 mL of distilled water, adjusting it to pH6.5 to 7 by adding 16.4 mL of 0.1M sodium hydroxide solution thereto, and freeze-drying it to obtain a sodium salt thereof. Further, the used compound was also prepared as follows. 500 mg of the compound No. 7 described in Synthetic Example 7 of Example I was suspended in 5 mL of distilled water. 1.61 mL of 1M sodium hydroxide and 0.8 mL of 2M hydrochloric acid were added thereto at 0° C. respectively to precipitate a solid substance. The precipitated solid substance was taken by filtration and dried under reduced pressure at 40° C. to obtain 426 mg of the compound No. 7. The obtained solid substance was suspended in 10 mL of distilled water. 1.2 mL of 1M sodium hydroxide was added thereto and freeze-dried to obtain a sodium salt thereof. The compound No. 21 was used in the form of a sodium salt of the compound No. 21 described in Synthetic Example 21 of Example I, which was prepared by the same method as mentioned above.

A quantitative sensory evaluation test was conducted as follows. 0.000001 to 0.1 g/dL of the compound(s) (a sodium salt of No. 1) was mixed as a sample to distilled water containing glutamic sodium (0.05 g/dL), inosine monophosphate (0.05 g/dL) and sodium chloride (0.5 g/dL). Then, the intensity of kokumi-imparting activity was examined at that time. As a reference, γGlu-Cys-Gly and γGlu-Val-Gly were used, each of which is a known kokumi-imparting component. As for a sample that becomes acidic to an additive-free control after dissolving the sample, it was used by being adjusted with sodium hydroxide to become within pH±0.2 to the additive-free control. As for sensory scoring, it was defined as a control: 0, strong: 3, and very strong: 5; and n=4. Meanwhile, "first-middle taste" means the taste combining first taste and middle taste. The kokumi-imparting activity was widely seen in the above addition concentrations, and the results of the representative concentrations are shown in Table 5.

TABLE 5

| Sample | Conc. (g/dL) | Intensity of kokumi First-middle taste | After taste | Comments |
|---|---|---|---|---|
| Control | — | 0 | 0 | — |
| γ Glu-Cys-Gly | 0.01 | 3.0 | 3.0 | Richness, thickness and continuity become stronger. |

TABLE 5-continued

| Sample | Conc. (g/dL) | Intensity of kokumi First-middle taste | After taste | Comments |
|---|---|---|---|---|
| γ Glu-Val-Gly | 0.001 | 2.5 | 3.0 | Mellowness, richness and growth (mouthfullness) become mainly stronger. |
|  | 0.005 | 3.5 | 4.0 | Mellowness, richness and growth (mouthfullness) become mainly stronger. |
| No. 1-Na salt | 0.00001 | 0.7 | 1.0 | Though there is thickness, it is not enough. |
|  | 0.0001 | 1.8 | 2.0 | There is a harmony and a bit of thickness. |
|  | 0.0005 | 2.6 | 3.0 | There is a harmony, richness and thickness. |
|  | 0.001 | 3.2 | 3.6 | All tastes are strong, mainly thickness and continuity. |
|  | 0.01 | 5.0 | 5.0 | All tastes are strong. |
| No. 7-Na salt | 0.00005 | 2.2 | 2.5 | Thickness is felt mainly in the middle taste. |
|  | 0.0001 | 2.5 | 3.2 | There is about the same thickness as that of 0.001 γ Glu-Val-Gly. |
|  | 0.0005 | 3.3 | 4.0 | Strong thickness is felt from the middle taste. It has a strong after taste. |
| No. 21-Na salt | 0.0002 | 1.5 | 2.0 | Richness is somewhat felt, but weak. |
|  | 0.0005 | 2.6 | 3.1 | Richness is felt. Umami and sweetness become stronger. |
|  | 0.001 | 3.1 | 3.7 | Though richness is strong, there is some bitterness and tastes are vague. |

What is claimed is:

1. A glutamic acid derivative of formula (I) or a pharmaceutically acceptable thereof:

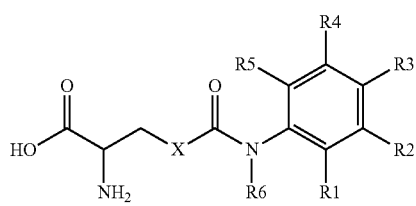

(I)

wherein $R_1$ and $R_3$-$R_5$ are each independently selected from the group consisting of a hydrogen atom, a halogeno group, a hydroxyl group, a nitro group, —$NH_2$, an optionally substituted alkyl group having 1 to 6 carbon atoms, and an optionally substituted alkoxy group having 1 to 6 carbon atoms;

$R_2$ is selected from the group consisting of a nitro group, a sulfonic acid group,

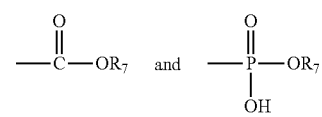

$R_6$ is a hydroxyl group;

$R_7$ is a hydrogen atom or an optionally substituted alkyl group having 1 to 6 carbon atoms; and X is a methylene group or an oxygen atom.

2. A pharmaceutical composition comprising a glutamic acid derivative of formula (I) or a pharmaceutically acceptable salt thereof:

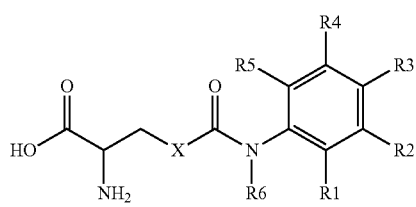

(I)

wherein $R_1$ and $R_3$-$R_5$ are each independently selected from the group consisting of a hydrogen atom, a halogeno group, a hydroxyl group, —$NH_2$, an optionally substituted alkyl group having 1 to 6 carbon atoms, and an optionally substituted alkoxy group having 1 to 6 carbon atoms;

$R_2$ is selected from the group consisting of a sulfonic acid group,

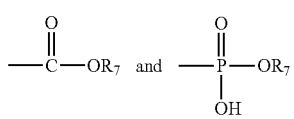

$R_6$ and $R_7$ are each independently a hydrogen atom or an optionally substituted alkyl group having 1 to 6 carbon atoms; and X is a methylene group or an oxygen atom, and excluding a compound wherein X is a methylene group, $R_2$ is

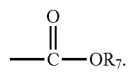

3. A pharmaceutical composition comprising the glutamic acid derivative or pharmaceutically acceptable salt thereof according to claim 1 and a pharmaceutically acceptable carrier.

4. The glutamic acid derivative or pharmaceutically acceptable salt thereof of claim 1, wherein X is methylene.

5. The glutamic acid derivative or pharmaceutically acceptable salt thereof of claim 2, wherein X is methylene.

* * * * *